(12) United States Patent
Shimizu et al.

(10) Patent No.: US 10,428,004 B2
(45) Date of Patent: Oct. 1, 2019

(54) METHOD FOR PRODUCING ACETIC ACID

(71) Applicant: DAICEL CORPORATION, Osaka-shi, Osaka (JP)

(72) Inventors: Masahiko Shimizu, Himeji (JP); Yoshihisa Mizutani, Himeji (JP)

(73) Assignee: DAICEL CORPORATION, Osaka-shi, Osaka (JP)

( * ) Notice: Subject to any disclaimer, the term of this patent is extended or adjusted under 35 U.S.C. 154(b) by 0 days.

(21) Appl. No.: 15/540,195

(22) PCT Filed: May 25, 2017

(86) PCT No.: PCT/JP2017/019574
§ 371 (c)(1),
(2) Date: Jun. 27, 2017

(87) PCT Pub. No.: WO2018/135015
PCT Pub. Date: Jul. 26, 2018

(65) Prior Publication Data
US 2018/0201564 A1 Jul. 19, 2018

(30) Foreign Application Priority Data

Jan. 18, 2017 (JP) .................. 2017-006646
Mar. 2, 2017 (JP) .................. 2017-039390

(51) Int. Cl.
C07C 51/12 (2006.01)
C07C 51/44 (2006.01)
B01D 3/00 (2006.01)
B01D 3/14 (2006.01)
B01D 15/36 (2006.01)

(52) U.S. Cl.
CPC ............. C07C 51/12 (2013.01); B01D 3/009 (2013.01); B01D 3/143 (2013.01); B01D 15/361 (2013.01); C07C 51/44 (2013.01); C07C 51/445 (2013.01); Y02P 20/127 (2015.11)

(58) Field of Classification Search
USPC ........................................ 562/529
See application file for complete search history.

(56) References Cited

U.S. PATENT DOCUMENTS

| | | | |
|---|---|---|---|
| 3,772,156 A | 11/1973 | Johnson et al. | |
| 4,029,553 A | 6/1977 | Price | |
| 5,916,422 A * | 6/1999 | Kimura | C07C 51/44 203/16 |
| 6,143,930 A | 11/2000 | Singh et al. | |
| 6,458,996 B1 | 10/2002 | Muskett | |
| 2005/0197508 A1 | 9/2005 | Scates et al. | |
| 2005/0197509 A1 | 9/2005 | Picard et al. | |
| 2005/0197513 A1 | 9/2005 | Trueba et al. | |
| 2007/0093676 A1 | 4/2007 | Kojima et al. | |
| 2010/0145097 A1 | 6/2010 | Brtko et al. | |
| 2013/0264186 A1 | 10/2013 | Shimizu et al. | |
| 2015/0025270 A1 | 1/2015 | Shimizu et al. | |

FOREIGN PATENT DOCUMENTS

| | | |
|---|---|---|
| EP | 0976711 A1 | 2/2000 |
| EP | 2657220 A1 | 10/2013 |
| EP | 2826767 A1 | 1/2015 |
| JP | 48-61414 A | 8/1973 |
| JP | 52-17413 A | 2/1977 |
| JP | 2000-53609 A | 2/2000 |
| JP | 2001-508405 A | 6/2001 |
| JP | 2005-289936 A | 10/2005 |
| JP | 2006-182691 A | 7/2006 |
| JP | 2007-526305 A | 9/2007 |
| JP | 2007-526306 A | 9/2007 |
| JP | 2007-526310 A | 9/2007 |
| JP | 2014-500255 A | 1/2014 |
| WO | WO 98/17619 A2 | 4/1998 |
| WO | WO 2005/085166 A1 | 9/2005 |
| WO | WO 2005/087698 A1 | 9/2005 |
| WO | WO 2005/087699 A1 | 9/2005 |
| WO | WO 2010/077261 A1 | 7/2010 |
| WO | WO 2012/064832 A1 | 5/2012 |
| WO | WO 2012/086386 A1 | 6/2012 |
| WO | WO 2013/137236 A1 | 9/2013 |
| WO | WO 2016/194850 A1 | 12/2016 |
| WO | WO 2017/057085 A1 | 4/2017 |
| WO | WO 2017/057142 A1 | 4/2017 |

OTHER PUBLICATIONS

English translation of Written Opinion dated Nov. 17, 2017, in PCT International Application No. PCT/JP2017/019574.
Written Opinion of the International Searching Authority and International Search Report (forms PCT/ISA/237 and PCT/ISA/210), dated Aug. 22, 2017, for International Application No. PCT/JP2017/019574.
Japanese Notification of Reasons for Rejection for Application No. 2017-533363, dated Jun. 26, 2018, with English language translation.

* cited by examiner

Primary Examiner — Ana Z Muresan
(74) Attorney, Agent, or Firm — Birch, Stewart, Kolasch & Birch, LLP

(57) ABSTRACT

It is intended to provide a method capable of suppressing distillation apparatus corrosion as a method for producing acetic acid, comprising the step of distilling a crude acetic acid solution containing acetic acid and an impurity having a higher boiling point than that of acetic acid to purify the acetic acid. The method for producing acetic acid of the present invention comprises the step described above, wherein the distillation of the crude acetic acid solution is performed under a condition involving a distillation column bottom temperature of not more than 165° C. An acetic acid concentration in the crude acetic acid solution to be subjected to the distillation is preferably not less than 90 mass %. Examples of the impurity having a higher boiling point than that of acetic acid include acetate salts, acetic anhydride, and propionic acid. A column bottom pressure of the distillation column is preferably less than 0.255 MPaG.

20 Claims, 5 Drawing Sheets

[Figure 1]
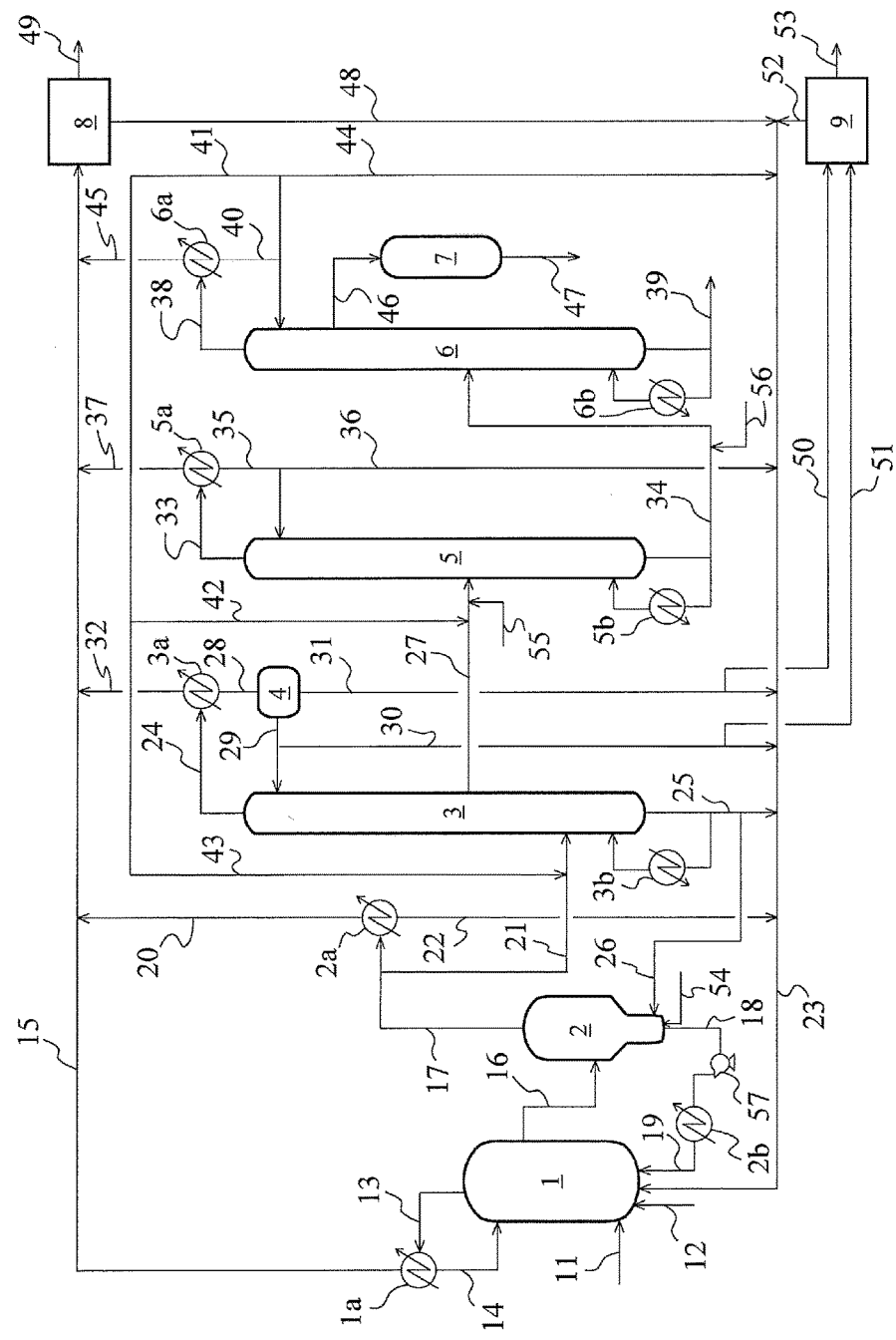

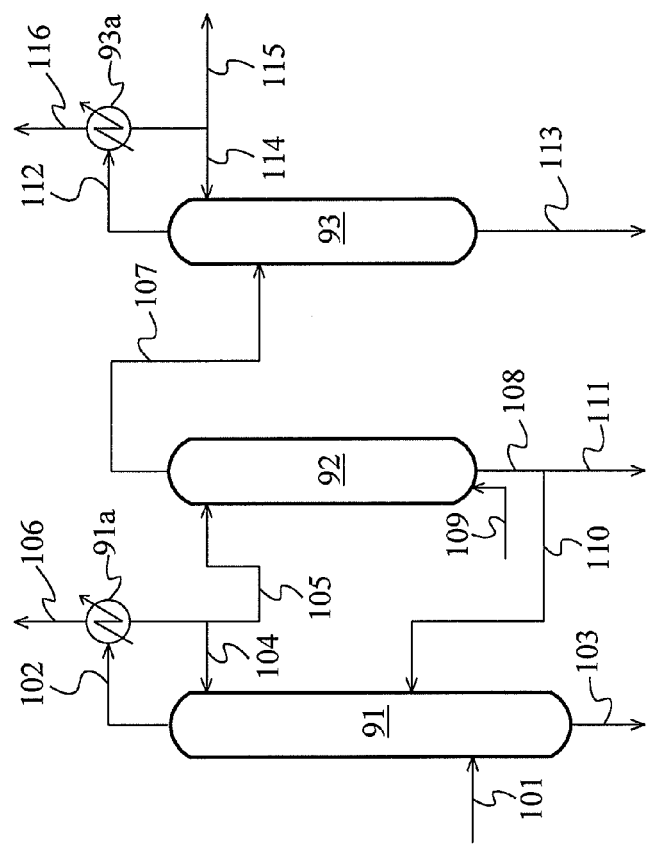
[Figure 2]

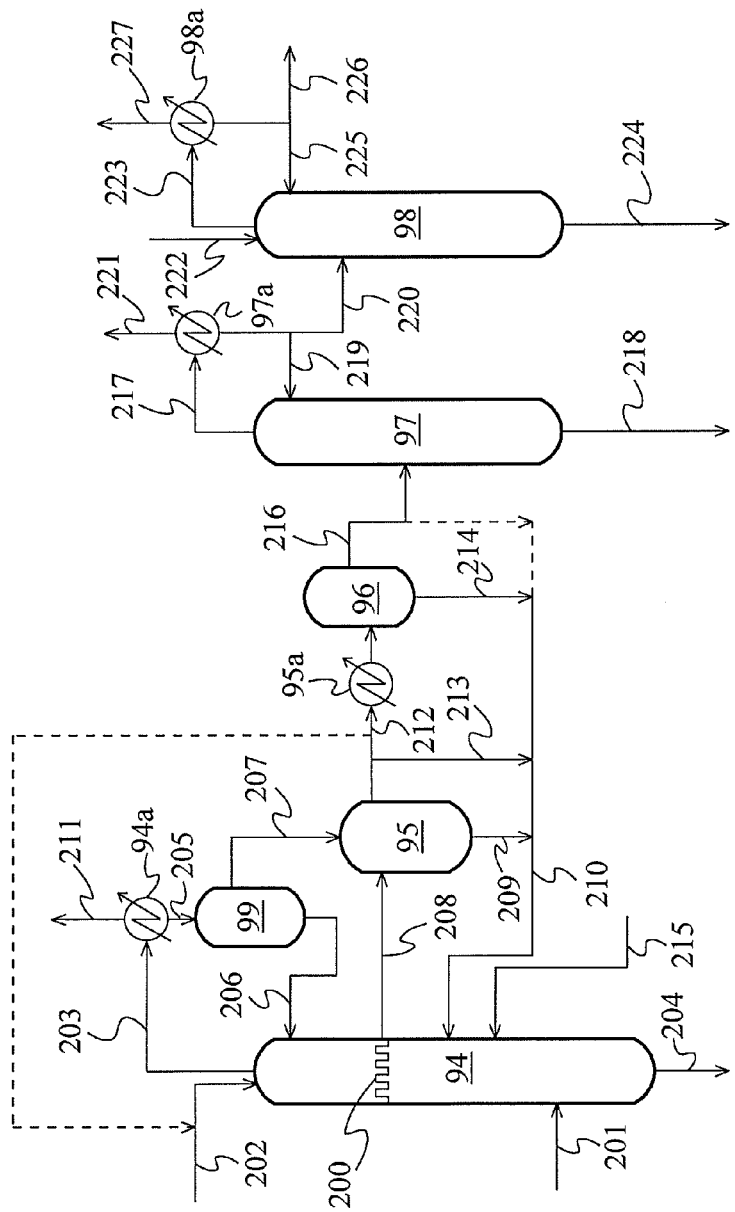
[Figure 3]

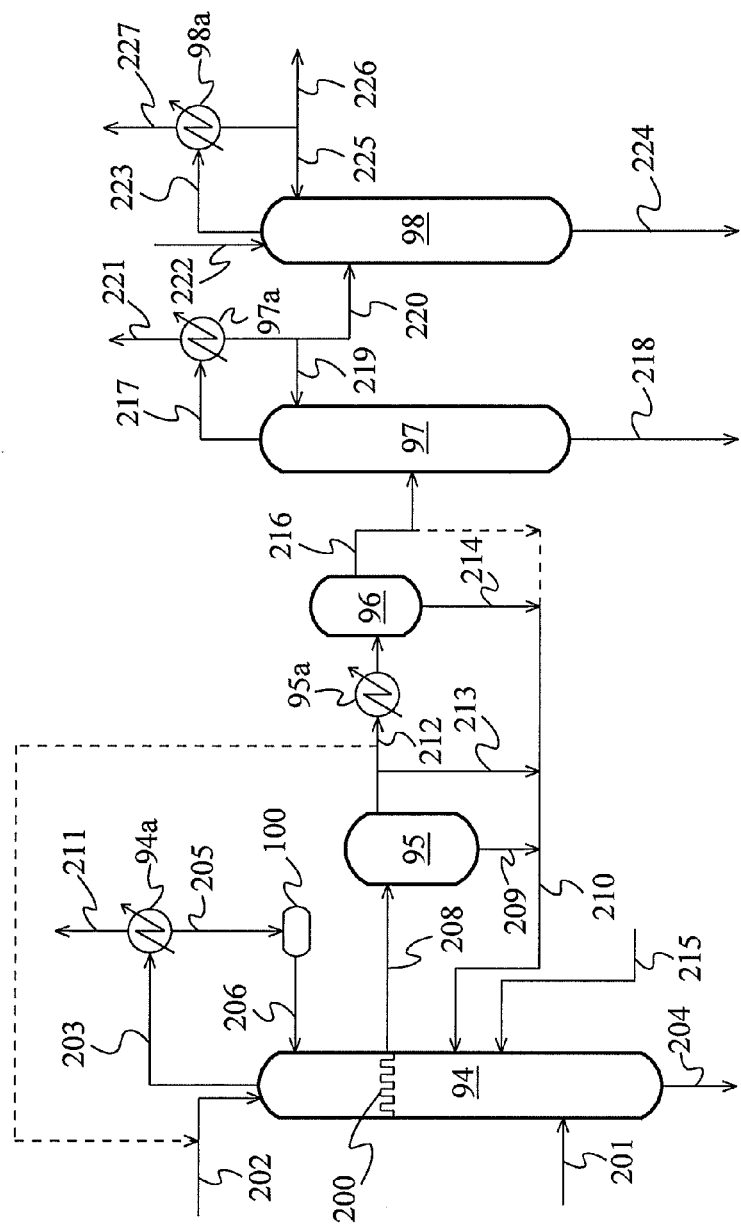
[Figure 4]

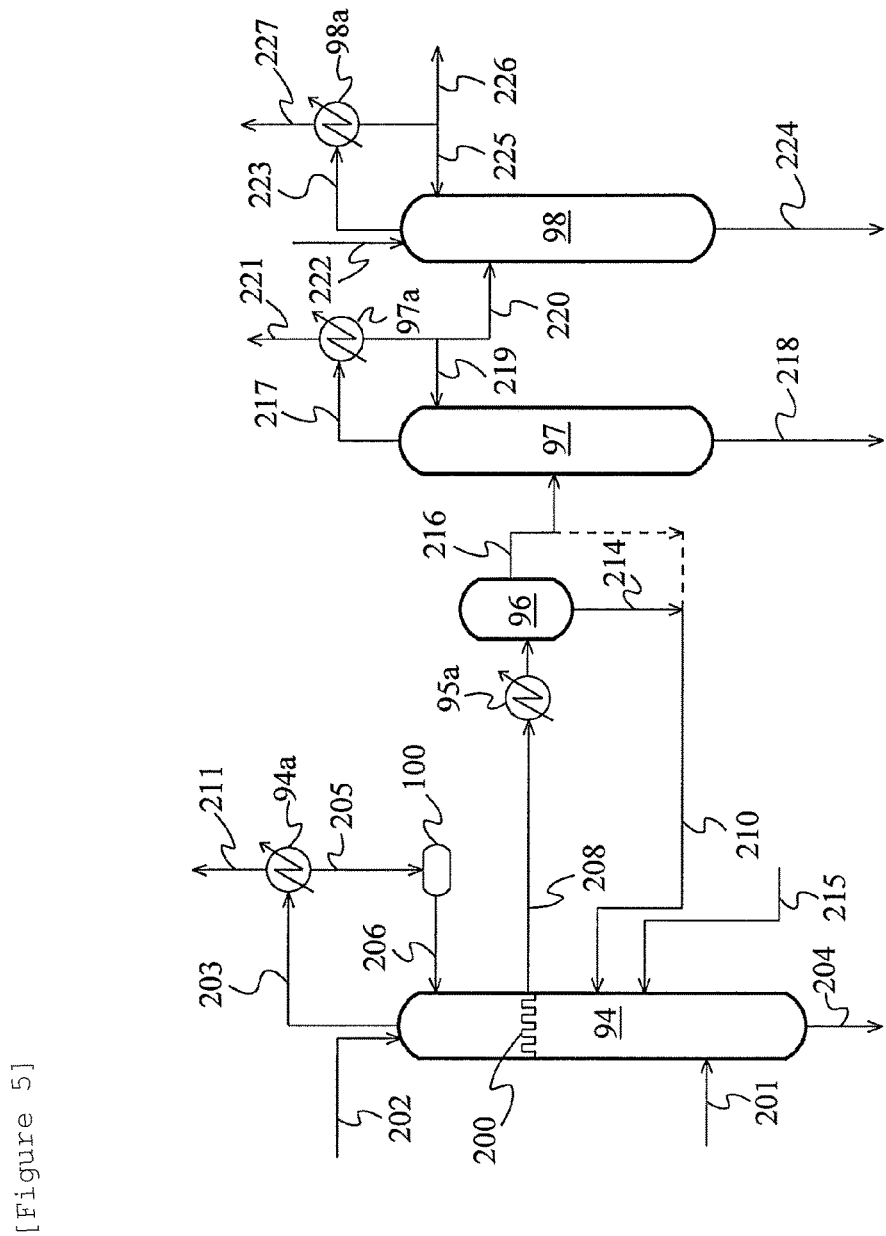
[Figure 5]

METHOD FOR PRODUCING ACETIC ACID

TECHNICAL FIELD

The present invention relates to a method for producing acetic acid. The present application claims the priorities of Japanese Patent Application No. 2017-006646 filed in Japan on Jan. 18, 2017 and Japanese Patent Application No. 2017-039390 filed in Japan on Mar. 2, 2017, the contents of which are incorporated herein by reference in their entirety.

BACKGROUND ART

A carbonylation process of a methanol method is known as an industrial method for producing acetic acid. In this process, for example, methanol and carbon monoxide are reacted in the presence of a catalyst in a reaction vessel to produce acetic acid. The reaction mixture is evaporated in an evaporator, and the vapor phase is purified in a lower boiling point component removal column and subsequently in a dehydration column so that product acetic acid is prepared. Alternatively, product acetic acid is prepared via a higher boiling point component removal column subsequent to the dehydration column, and further, a product column (Patent Literature 1, etc.).

In such an acetic acid production process, a distillation column for distilling a crude acetic acid solution containing acetic acid and an impurity having a higher boiling point than that of acetic acid to purify the acetic acid, for example, the dehydration column, the higher boiling point component removal column, or the product column described above, presents the significant problem that the apparatus is corroded. Therefore, an expensive material having corrosion resistance is used, or a corroded part needs to be repaired, leading to increase in equipment cost or maintenance cost.

CITATION LIST

Patent Literature

Patent Literature 1: Japanese Patent Laid-Open No. 2006

SUMMARY OF INVENTION

Technical Problem

Thus, an object of the present invention is to provide a method capable of suppressing the corrosion of a distillation apparatus as a method for producing acetic acid, comprising the step of distilling a crude acetic acid solution containing acetic acid and an impurity having a higher boiling point than that of acetic acid to purify the acetic acid.

Solution to Problem

In order to attain the object, the present inventors have first studied the association of the composition of a column bottom fraction of a distillation column with a column bottom temperature.

In the carbonylation process of the methanol method, a metal catalyst such as a rhodium catalyst is used as a catalyst, and methyl iodide is used as a co-catalyst. Therefore, hydrogen iodide is produced as a by-product in the reaction system. Although methyl iodide and hydrogen iodide are mostly separated by distillation in a dehydration column, hydrogen iodide of a ppb or ppm order is present in a bottom fraction of the dehydration column. Therefore, an alkali such as potassium hydroxide is fed into the column interior or the bottom fraction of the dehydration column to neutralize the residual hydrogen iodide. The formed alkali metal salts (alkali metal iodides and alkali metal acetates) are removed in distillation equipment or the like (e.g., a higher boiling point component removal column) in the next step. Such alkali metal salts are concentrated at the bottom of the distillation column and discarded, together with acetic acid, from a bottom line. However, the amount of these alkali metal salts discarded is minimized for improvement in acetic acid use rate. Therefore, an alkali metal salt concentration in a column bottom fraction of the distillation column is increased, and a rise in boiling point caused by the salts occurs so that the column bottom temperature (bottom temperature) of the distillation column is elevated.

Since water is hardly present at the bottom of the distillation column (e.g., a higher boiling point component removal column) described above, acetic anhydride is formed through the dehydration reaction of acetic acid. This acetic anhydride is formed in a large amount by the catalytic effect of a metal iodide (e.g., iron iodide), if any, generated by the corrosion of distillation equipment by hydrogen iodide. In the case of providing an ion exchange resin treatment step in an acetic acid purification step, dehydration reaction mediated by an acid catalyst is accelerated to increase acetic anhydride if a portion of a resin, a sulfonic acid group, or the like is eliminated. Thus, in the case of disposing a distillation column (e.g., a product column) for purifying acetic acid downstream of the ion exchange resin treatment step, acetic anhydride is present in a large amount in a column bottom fraction of this distillation column so that the column bottom temperature is elevated.

Furthermore, higher boiling point impurities, such as propionic acid, which are produced as by-products in the reaction system are concentrated at the bottom of the distillation column. This is also partly responsible for a rise in column bottom temperature.

Next, on the basis of these studies and discussions, the present inventors have examined, by a corrosion test, the association of the types and amounts of higher boiling point impurities present in a column bottom fraction of the distillation column, a column bottom temperature and pressure, and the corrosiveness of various materials. As a result, the present inventors have gained the findings that: the corrosion rate is remarkably influenced by a temperature; only a highly durable material such as zirconium, or Hastelloy B2 among nickel-based alloys can be used at a temperature of not less than 160° C.; even for pure acetic acid, the corrosion rate is increased as the boiling point is elevated by a rise in pressure; under the same operating pressure, the corrosion rate is increased with increase in the concentration of potassium acetate, acetic anhydride, or propionic acid resulting in a rise in boiling point; the corrosion rate differs depending on the types of higher boiling point impurities; etc. The present invention is based on these findings and has been completed through further studies.

Specifically, the present invention provides a method for producing acetic acid, comprising the step of distilling a crude acetic acid solution containing acetic acid and an impurity having a higher boiling point than that of acetic acid to purify the acetic acid, wherein the distillation of the crude acetic acid solution is performed under a condition involving a column bottom temperature of a distillation column of not more than 165° C.

It is preferred that an acetic acid concentration in the crude acetic acid solution should be not less than 90% by mass.

It is preferred that the impurity having a higher boiling point than that of acetic acid should comprise at least one compound selected from the group consisting of, for example, an acetate salt, acetic anhydride, and propionic acid.

It is preferred that an acetate salt concentration of a column bottom fraction of the distillation column should be not more than 34% by mass.

It is preferred that an acetic anhydride concentration of the column bottom fraction of the distillation column should be not more than 90% by mass.

It is preferred that a propionic acid concentration of the column bottom fraction of the distillation column should be not more than 90% by mass.

It is preferred that the distillation should be performed under a condition involving a column bottom pressure of the distillation column of less than 0.255 MPaG.

It is preferred that the distillation should be performed under a condition involving a column bottom pressure of the distillation column of not less than 0.01 MPaG and less than 0.255 MPaG.

It is preferred that the production method should comprise a carbonylation reaction step of reacting methanol with carbon monoxide to produce acetic acid, an evaporation step of separating the reaction mixture obtained in the carbonylation reaction step into a vapor stream and a residual liquid stream, a lower boiling point component removal step of separating the vapor stream by distillation into an overhead stream rich in lower boiling point component and an acetic acid stream rich in acetic acid, and an acetic acid distillation step of distilling the acetic acid stream to purify the acetic acid, wherein the acetic acid distillation step has at least one step of performing the distillation of the crude acetic acid solution under a condition involving a column bottom temperature of the distillation column of not more than 165° C. In this case, it is preferred that the acetic acid distillation step should have at least one distillation step in which an acetic acid concentration in the crude acetic acid solution to be subjected to the distillation is not less than 97% by mass, and in all of such steps, the distillation of the crude acetic acid solution should be performed under a condition involving a column bottom temperature of the distillation column of not more than 165° C.

It is preferred that a material for the distillation column should be at least one material selected from the group consisting of a nickel-based alloy, stainless steel, aluminum, and titanium.

In the production method, it is preferred that the column bottom fraction of the distillation column should have an acetate salt concentration of not more than 34% by mass, an acetic anhydride concentration of not more than 90% by mass, and a propionic acid concentration of not more than 90% by mass, the column bottom pressure of the distillation column should be less than 0.255 MPa, the material for the distillation column should be at least one material selected from the group consisting of a nickel-based alloy, stainless steel, aluminum, and titanium, and the column bottom temperature should be less than 165° C.

Advantageous Effects of Invention

According to the present invention, a crude acetic acid solution containing acetic acid and an impurity having a higher boiling point than that of acetic acid is distilled to purify the acetic acid. This distillation is performed under a condition involving a column bottom temperature of a distillation column of not more than 165° C. Therefore, the corrosion of the distillation column can be significantly suppressed even in the case of performing the distillation under increased pressure for improvement in acetic acid production efficiency.

BRIEF DESCRIPTION OF DRAWINGS

FIG. 1 is an acetic acid production flow diagram showing one embodiment of the present invention.

FIG. 2 is a schematic flow diagram showing one example of an acetaldehyde separation and removal system.

FIG. 3 is a schematic flow diagram showing another example of the acetaldehyde separation and removal system.

FIG. 4 is a schematic flow diagram showing a further alternative example of the acetaldehyde separation and removal system.

FIG. 5 is a schematic flow diagram showing a further alternative example of the acetaldehyde separation and removal system.

DESCRIPTION OF EMBODIMENTS

In the method for producing acetic acid according to the present invention, a crude acetic acid solution containing acetic acid and an impurity having a higher boiling point than that of acetic acid is distilled to purify the acetic acid. In this operation, a column bottom temperature of a distillation column is set to not more than 165° C. (e.g., less than 165° C.). The column bottom temperature refers to the temperature of a column bottom fraction. The column bottom temperature of the distillation column is set to not more than 165° C. (e.g., less than 165° C.), whereby the corrosion of the distillation column apparatus can be significantly suppressed. Therefore, even a material that is not a material having high corrosion resistance (zirconium, etc.) can be used as a material for the distillation column. If the column bottom temperature of the distillation column is more than 165° C., the corrosion rates of stainless steel and some nickel-based alloys are fast even in the case where an acetate salt, acetic anhydride, and propionic acid are absent in the column bottom fraction. These materials are unsuitable as materials for the distillation column apparatus.

The column bottom temperature of the distillation column is preferably not more than 160° C., more preferably not more than 155° C., further preferably not more than 150° C., particularly preferably not more than 140° C. When the column bottom temperature of the distillation column is not more than 160° C., particularly not more than 155° C., stainless steel can be used as a material for the distillation apparatus even if an acetate salt, acetic anhydride, and propionic acid are present in considerable amounts in the column bottom fraction. When the column bottom temperature of the distillation column is not more than 155° C., particularly not more than 150° C., corrosion can be significantly suppressed even if the material for the distillation apparatus is stainless steel. The lower limit of the column bottom temperature is, for example, 125° C., preferably 130° C., further preferably 135° C.

The crude acetic acid solution to be subjected to the distillation can contain acetic acid and an impurity having a higher boiling point than that of acetic acid and preferably contains acetic acid as a main component. An acetic acid concentration in the crude acetic acid solution is preferably not less than 90% by mass (e.g., not less than 95% by mass), more preferably not less than 97% by mass, further preferably not less than 98% by mass, particularly preferably not less than 99% by mass.

The impurity having a higher boiling point than that of acetic acid is not particularly limited, and the present invention produces great effects, particularly, in the case where at least one compound selected from the group consisting of an acetate salt, acetic anhydride, and propionic acid is contained as the higher boiling point impurity. Examples of the acetate salt include alkali metal acetates such as potassium acetate.

An acetate salt concentration in the column bottom fraction of the distillation column is, for example, not more than 34% by mass, preferably not more than 23% by mass, more preferably not more than 13% by mass, further preferably not more than 10% by mass, particularly preferably not more than 1% by mass. As the acetate salt concentration in the column bottom fraction is lower, the corrosion rate is slower. The lower limit of the acetate salt concentration in the column bottom fraction is, for example, 0 ppm by mass (or 1 ppm by mass). In the carbonylation process of the methanol method, as mentioned above, an alkali such as potassium hydroxide is added in order to neutralize highly corrosive hydrogen iodide produced as a by-product in a reaction system. The added alkali not only reacts with hydrogen iodide but reacts with acetic acid to form an acetate salt (e.g., potassium acetate). When the crude acetic acid solution containing such an acetate salt is distilled, the acetate is retained at the column bottom of the distillation column. Thus, the acetate salt concentration in the column bottom fraction of the distillation column can be adjusted, for example, by increasing or decreasing the amount of the alkali added.

An acetic anhydride concentration in the column bottom fraction of the distillation column is, for example, not more than 90% by mass, preferably not more than 74% by mass, more preferably not more than 45% by mass, further preferably not more than 10% by mass, particularly preferably not more than 1% by mass. As the acetic anhydride concentration in the column bottom fraction is lower, the corrosion rate is slower. The lower limit of the acetic anhydride concentration in the column bottom fraction is, for example, 0 ppm by mass (or 1 ppm by mass). The acetic anhydride concentration in the column bottom fraction of the distillation column can be adjusted, for example, by hydrolyzing the acetic anhydride by the addition of water into piping or an apparatus positioned upstream of the distillation column, or into the distillation column.

A propionic acid concentration in the column bottom fraction of the distillation column is, for example, not more than 90% by mass, preferably not more than 75% by mass, more preferably not more than 55% by mass, further preferably not more than 29% by mass, particularly preferably not more than 10% by mass (in particular, not more than 1% by mass). As the propionic acid concentration in the column bottom fraction is lower, the corrosion rate is slower. The lower limit of the propionic acid concentration in the column bottom fraction is, for example, 0 ppm by mass (or 1 ppm by mass). The propionic acid concentration in the column bottom fraction of the distillation column can be lowered by, for example, reduction in the production of the by-product propionic acid by changing reaction conditions, separation and removal of acetaldehyde responsible for the production of the by-product propionic acid from a process solution during recycle of a portion of the process solution to the reaction system, followed by recycle to the reaction system, or disposition of a distillation column or an evaporator (propionic acid removal column) for propionic acid separation and removal upstream of the distillation column.

A column bottom pressure of the distillation column is appropriately adjusted according to the desired column bottom temperature and composition of the column bottom fraction. The column bottom pressure is, for example, less than 0.255 MPaG, preferably not more than 0.24 MPaG, further preferably not more than 0.23 MPaG, particularly preferably not more than 0.21 MPaG. In this context, "G" represents gauge pressure. As the concentration of the higher boiling point impurity in the column bottom fraction is higher, the boiling point is higher. Therefore, for attaining the desired column bottom temperature, it is necessary to decrease the column bottom pressure with increase in the concentration of the higher boiling point impurity in the column bottom fraction. At a lower column bottom pressure, the column bottom temperature is decreased so that corrosiveness is reduced. However, since gas density is decreased at a lower column bottom pressure, this is economically disadvantageous because there arises the need of increasing the column diameter, etc., of the distillation column for maintaining the given amount of acetic acid produced. Thus, the lower limit of the column bottom pressure of the distillation column is, for example, 0.01 MPaG, preferably 0.02 MPaG, further preferably 0.03 MPaG, particularly preferably 0.05 MPaG. According to the present invention, the column bottom temperature is adjusted to not more than the specific value. Therefore, even under increased pressure, acetic acid can be purified by distillation while the corrosion of the apparatus is prevented. Thus, the present invention enhances acetic acid production efficiency and is therefore particularly useful in the case of performing the distillation under increased pressure.

In the present invention, zirconium, a nickel-based alloy (Hastelloy B2, Hastelloy C, etc.), stainless steel [e.g., SUS304, SUS316, SUS316L (SUS material having a lower carbon ratio than that of SUS316), SUS317, SUS317L (SUS material having a lower carbon ratio than that of SUS317), etc.], or a material having corrosion resistance (e.g., aluminum and titanium) equivalent to or lower than these materials can be used as a material for the distillation column. In general, the prices of these materials are decreased in the order of zirconium>Hastelloy B2>Hastelloy C>stainless steel. According to the present invention, the relatively inexpensive stainless steel can also be sufficiently used as a material for the distillation column because corrosion can be significantly reduced.

In the present invention, it is particularly preferred that the column bottom fraction of the distillation column should have an acetate salt concentration of not more than 34% by mass, an acetic anhydride concentration of not more than 90% by mass, and a propionic acid concentration of not more than 90% by mass, the column bottom pressure of the distillation column should be less than 0.255 MPa, and the material for the distillation column should be at least one material selected from the group consisting of a nickel-based alloy, stainless steel, aluminum, and titanium.

In the present invention, the format of the distillation may be any of batch distillation and continuous distillation, and continuous distillation is more preferred from the viewpoint of production efficiency, etc.

The method for producing acetic acid according to the present invention is particularly useful in the carbonylation process of the methanol method. Specifically, in an acetic acid production process comprising a carbonylation reaction step of reacting methanol with carbon monoxide to produce acetic acid, an evaporation step of separating the reaction mixture obtained in the carbonylation reaction step into a vapor stream and a residual liquid stream, a lower boiling point component removal step of separating the vapor stream by distillation into an overhead stream rich in lower boiling point component and an acetic acid stream rich in acetic acid, and an acetic acid distillation step of distilling the acetic acid stream to purify the acetic acid, it is preferred that the acetic acid distillation step should have at least one step of distilling a crude acetic acid solution containing acetic acid and an impurity having a higher boiling point than that of acetic acid under a condition involving a column bottom temperature of the distillation column of not more than 165° C. to obtain purified acetic acid.

In this case, it is preferred that the acetic acid distillation step should have at least one distillation step in which an acetic acid concentration in the crude acetic acid solution to be subjected to the distillation is not less than 97% by mass, and in all of such steps, the crude acetic acid solution should be distilled under a condition involving a column bottom temperature of the distillation column of not more than 165° C. to obtain purified acetic acid.

Hereinafter, one embodiment of the present invention will be described. FIG. 1 is one example of an acetic acid production flow diagram (carbonylation process of a methanol method) showing one embodiment of the present invention. An acetic acid production apparatus associated with this acetic acid production flow has a reaction vessel 1, an evaporator 2, a distillation column 3, a decanter 4, a distillation column 5, a distillation column 6, an ion exchange resin column 7, a scrubber system 8, an acetaldehyde separation and removal system 9, condensers 1a, 2a, 3a, 5a, and 6a, a heat exchanger 2b, reboilers 3b, 5b, and 6b, lines 11 to 56, and a pump 57 and is configured to be capable of continuously producing acetic acid. In the method for producing acetic acid according to the present embodiment, a reaction step, an evaporation step (flash step), a first distillation step, a second distillation step, a third distillation step, and an adsorptive removal step are performed in the reaction vessel 1, the evaporator 2, the distillation column 3, the distillation column 5, the distillation column 6, and the ion exchange resin column 7, respectively. The first distillation step is also referred to as a lower boiling point component removal step, the second distillation step is also referred to as a dehydration step, and the third distillation step is also referred to as a higher boiling point component removal step. The first distillation step, the second distillation step, and the third distillation step are included in the "acetic acid distillation step to purify the acetic acid" according to the present invention. In the present invention, the steps are not limited to those described above and may exclude, particularly, equipment of the distillation column 5, the ion exchange resin column 7 and the acetaldehyde separation and removal system 9 (acetaldehyde removal column, etc.). As mentioned later, a product column may be disposed downstream of the ion exchange resin column 7. This product column is also included in the "acetic acid distillation step to purify the acetic acid" according to the present invention.

The reaction vessel 1 is a unit for performing the reaction step. This reaction step is a step for continuously producing acetic acid through a reaction (methanol carbonylation reaction) represented by the chemical formula (1) given below. In a steady operation state of the acetic acid production apparatus, for example, a reaction mixture under stirring with a stirrer is present in the reaction vessel 1. The reaction mixture contains methanol and carbon monoxide which are raw materials, a metal catalyst, a co-catalyst, water, a production target acetic acid, and various by-products, and a liquid phase and a gaseous phase are in equilibrium.

$$CH_3OH + CO \rightarrow CH_3COOH \quad (1)$$

The raw materials in the reaction mixture are methanol in a liquid state and carbon monoxide in a gaseous state. Methanol is continuously fed at a predetermined flow rate to the reaction vessel 1 from a methanol reservoir (not shown) through the line 11. Carbon monoxide is continuously fed at a predetermined flow rate to the reaction vessel 1 from a carbon monoxide reservoir (not shown) through the line 12. The carbon monoxide is not necessarily required to be pure carbon monoxide and may contain, for example, other gases such as nitrogen, hydrogen, carbon dioxide, and oxygen, in a small amount (e.g., not more than 5% by mass, preferably not more than 1% by mass).

The metal catalyst in the reaction mixture promotes the carbonylation reaction of methanol, and, for example, a rhodium catalyst or an iridium catalyst can be used. For example, a rhodium complex represented by the chemical formula $[Rh(CO)_2I_2]^-$ can be used as the rhodium catalyst. For example, an iridium complex represented by the chemical formula $[Ir(CO)_2I_2]^-$ can be used as the iridium catalyst. A metal complex catalyst is preferred as the metal catalyst. The concentration (based on the metal) of the catalyst in the reaction mixture is, for example, 200 to 5000 ppm by mass, preferably 400 to 2000 ppm by mass, with respect to the whole liquid phase of the reaction mixture.

The co-catalyst is an iodide for assisting the action of the catalyst mentioned above, and, for example, methyl iodide or an ionic iodide is used. The methyl iodide can exhibit the effect of promoting the catalytic effect of the catalyst mentioned above. The concentration of the methyl iodide is, for example, 1 to 20% by mass with respect to the whole liquid phase of the reaction mixture. The ionic iodide is an iodide that generates iodide ions in a reaction solution (particularly, an ionic metal iodide) and can exhibit the effect of stabilizing the catalyst mentioned above and the effect of suppressing side reaction. Examples of the ionic iodide include alkali metal iodides such as lithium iodide, sodium iodide, and potassium iodide. The concentration of the ionic iodide in the reaction mixture is, for example, 1 to 25% by mass, preferably 5 to 20% by mass, with respect to the whole liquid phase of the reaction mixture. In addition, when an iridium catalyst or the like is used, for example, a ruthenium compound or an osmium compound can be used as a co-catalyst. The amount of these compounds to be used as the total amount is, for example 0.1 to 30 moles (in terms of metal), preferably 0.5 to 15 moles (in terms of metal) based on 1 mole of iridium (in terms of metal).

Water in the reaction mixture is a component necessary for generating acetic acid in the reaction mechanism of the methanol carbonylation reaction and is also a component necessary for solubilizing a water-soluble component in the reaction system. The concentration of water in the reaction mixture is, for example, 0.1 to 15% by mass, preferably 0.8 to 10% by mass, further preferably 1 to 6% by mass, particularly preferably 1.5 to 4% by mass, with respect to the whole liquid phase of the reaction mixture. The water concentration is preferably not more than 15% by mass for pursuing efficient acetic acid production by reducing energy required for the removal of water in the course of purification of acetic acid. In order to control the water concentration, water may be continuously fed at a predetermined flow rate to the reaction vessel 1.

The acetic acid in the reaction mixture includes acetic acid fed in advance into the reaction vessel 1 before operation of the acetic acid production apparatus, and acetic acid generated as a main product of the methanol carbonylation reaction. Such acetic acid can function as a solvent in the reaction system. The concentration of the acetic acid in the reaction mixture is, for example, 50 to 90% by mass, preferably 60 to 80% by mass, with respect to the whole liquid phase of the reaction mixture.

Examples of the main by-products contained in the reaction mixture include methyl acetate. This methyl acetate may be generated through the reaction between acetic acid and methanol. The concentration of the methyl acetate in the reaction mixture is, for example, 0.1 to 30% by mass, preferably 1 to 10% by mass, with respect to the whole liquid phase of the reaction mixture. Another example of the by-products contained in the reaction mixture includes hydrogen iodide. This hydrogen iodide is inevitably generated under the reaction mechanism of the methanol carbonylation reaction in the case where the catalyst or the co-catalyst as mentioned above is used. The concentration of the hydrogen iodide in the reaction mixture is, for example, 0.01 to 2% by mass with respect to the whole liquid phase of the reaction mixture. Other examples of the by-products include hydrogen, methane, carbon dioxide, acetaldehyde, crotonaldehyde, 2-ethyl crotonaldehyde, dimethyl ether, alkanes, formic acid, propionic acid, and alkyl iodides such as hexyl iodide and decyl iodide. Also, the reaction mixture may contain a metal, such as iron, nickel, chromium, manganese, or molybdenum, generated by the corrosion of the apparatus (hereinafter, also referred to as a "corroded metal"), and other metals such as cobalt, zinc, and copper. The corroded metal and other metals are also collectively referred to as a "corroded metal, etc.".

In the reaction vessel 1 where the reaction mixture as described above is present, the reaction temperature is set to, for example, 150 to 250° C. The reaction pressure as the total pressure is set to, for example, 2.0 to 3.5 MPa (absolute pressure), and the carbon monoxide partial pressure is set to, for example, 0.4 to 1.8 MPa (absolute pressure), preferably 0.6 to 1.5 MPa (absolute pressure).

The vapor of a gaseous phase portion in the reaction vessel 1 during apparatus operation contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, formic acid, and propionic acid. This vapor can be withdrawn from the reaction vessel 1 through the line 13. The internal pressure of the reaction vessel 1 can be controlled by the adjustment of the amount of the vapor withdrawn, and, for example, the internal pressure of the reaction vessel 1 is kept constant. The vapor withdrawn from the reaction vessel 1 is introduced to the condenser 1a.

The condenser 1a separates the vapor from the reaction vessel 1 into a condensate portion and a gaseous portion by cooling and partial condensation. The condensate portion contains, for example, methyl iodide, hydrogen iodide, water, methyl acetate, acetic acid, dimethyl ether, methanol, acetaldehyde, formic acid, and propionic acid and is introduced to the reaction vessel 1 from the condenser 1a through the line 14 and recycled. The gaseous portion contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid and is fed to the scrubber system 8 from the condenser 1a through the line 15. In the scrubber system 8, useful components (e.g., methyl iodide, water, methyl acetate, and acetic acid) are separated and recovered from the gaseous portion from the condenser 1a. In this separation and recovery, a wet method that is performed using an absorbing liquid for capturing the useful components in the gaseous portion is utilized in the present embodiment. An absorption solvent containing at least acetic acid and/or methanol is preferred as the absorbing liquid. The absorbing liquid may contain methyl acetate. For example, a condensate portion of a vapor from the distillation column 6 mentioned later can be used as the absorbing liquid. In the separation and recovery, a pressure swing adsorption method may be used. The separated and recovered useful components (e.g., methyl iodide) are introduced to the reaction vessel 1 from the scrubber system 8 through the recycle line 48 and recycled. A gas after the capturing of the useful components is discarded through the line 49. The gas discharged from the line 49 can be used as a CO source to be introduced to the bottom of the evaporator 2 mentioned later or the residual liquid stream recycle lines 18 and 19. As for treatment in the scrubber system 8 and subsequent recycle to the reaction vessel 1 and discarding, the same holds true for gaseous portions described later that are fed to the scrubber system 8 from other condensers. For the production method of the present invention, it is preferred to have a scrubber step of separating offgas from the process into a stream rich in carbon monoxide and a stream rich in acetic acid by absorption treatment with an absorption solvent containing at least acetic acid.

In the reaction vessel 1 during apparatus operation, as mentioned above, acetic acid is continuously produced. The reaction mixture containing such acetic acid is continuously withdrawn at a predetermined flow rate from the reaction vessel 1 and introduced to the next evaporator 2 through the line 16.

The evaporator 2 is a unit for performing the evaporation step (flash step). This evaporation step is a step for separating the reaction mixture continuously introduced to the evaporator 2 through the line 16 (reaction mixture feed line), into a vapor stream (volatile phase) and a residual liquid stream (low volatile phase) by partial evaporation. The evaporation may be caused by reducing the pressure without heating the reaction mixture, or the evaporation may be caused by reducing the pressure while heating the reaction mixture. In the evaporation step, the temperature of the vapor stream is, for example, 100 to 260° C., preferably 120 to 200° C., and the temperature of the residual liquid stream is, for example, 80 to 200° C., preferably 100 to 180° C. The internal pressure of the evaporator is, for example, 50 to 1000 kPa (absolute pressure). The ratio between the vapor stream and the residual liquid stream to be separated in the evaporation step is, for example, 10/90 to 50/50 (vapor stream/residual liquid stream) in terms of a mass ratio. The vapor generated in this step contains, for example, methyl iodide, hydrogen iodide, water, methyl acetate, acetic acid, dimethyl ether, methanol, acetaldehyde, formic acid, and propionic acid and is continuously withdrawn to the line 17 (vapor stream discharge line) from the evaporator 2. A portion of the vapor stream withdrawn from the evaporator 2 is continuously introduced to the condenser 2a, and another portion of the vapor stream is continuously introduced to the next distillation column 3 through the line 21. The vapor stream has an acetic acid concentration of, for example, 40 to 85% by mass (preferably 50 to 85% by mass), further preferably 50 to 75% by mass (e.g., 55 to 75% by mass), a methyl iodide concentration of, for example, 2 to 50% by mass (preferably 5 to 30% by mass), a water concentration of, for example, 0.2 to 20% by mass (preferably 1 to 15% by mass), and a methyl acetate concentration of, for example, 0.2 to 50% by mass (preferably 2 to 30% by mass). The residual liquid stream generated in this step contains, for example, the catalyst and the co-catalyst (methyl iodide, lithium iodide, etc.) contained in the reaction mixture, and water, methyl acetate, acetic acid, formic acid, and propionic acid remaining without being volatilized in this step, and is continuously introduced to the heat exchanger 2b from the evaporator 2 through the line 18 using the pump 57. The heat exchanger 2b cools the residual liquid stream from the evaporator 2. The cooled residual liquid stream is continuously introduced to the reaction vessel 1 from the heat exchanger 2b through the line 19 and recycled. The line 18 and the line 19 are collectively referred to as residual liquid stream recycle lines. The acetic acid concentration of the residual liquid stream is, for example, 55 to 90% by mass, preferably 60 to 85% by mass.

The condenser 2a separates the vapor stream from the evaporator 2 into a condensate portion and a gaseous portion by cooling and partial condensation. The condensate portion contains, for example, methyl iodide, hydrogen iodide, water, methyl acetate, acetic acid, dimethyl ether, methanol, acetaldehyde, formic acid, and propionic acid and is introduced to the reaction vessel 1 from the condenser 2a through the lines 22 and 23 and recycled. The gaseous portion contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid and is fed to the scrubber system 8 from the condenser 2a through the lines 20 and 15. Since the reaction to produce acetic acid in the reaction step mentioned above is an exothermic reaction, a portion of heat accumulated in the reaction mixture is transferred to the vapor generated from the reaction mixture in the evaporation step (flash step). The condensate portion generated by the cooling of this vapor in the condenser 2a is recycled to the reaction vessel 1. Specifically, in this acetic acid production apparatus, heat generated through the methanol carbonylation reaction is efficiently removed in the condenser 2a.

The distillation column 3 is a unit for performing the first distillation step and serves as the so-called lower boiling point component removal column in the present embodiment. The first distillation step is the step of subjecting the vapor stream continuously introduced to the distillation column 3 to distillation treatment to separate and remove lower boiling point components. More specifically, in the first distillation step, the vapor stream is separated by distillation into an overhead stream rich in at least one lower boiling point component selected from methyl iodide and acetaldehyde, and an acetic acid stream rich in acetic acid. The distillation column 3 consists of, for example, a distillation column such as a plate column or a packed column. In the case of adopting a plate column as the distillation column 3, the theoretical number of plates thereof is, for example, 5 to 50, and the reflux ratio is, for example, 0.5 to 3000 according to the theoretical number of plates. In the inside of the distillation column 3, the column top pressure is set to, for example, 80 to 160 kPaG, and the column bottom pressure is higher than the column top pressure and is set to, for example, 85 to 180 kPaG. In the inside of the distillation column 3, the column top temperature is, for example, a temperature of lower than the boiling point of acetic acid at the set column top pressure and is set to 90 to 130° C., and the column bottom temperature is, for example, a temperature of not less than the boiling point of acetic acid at the set column bottom pressure and is set to 120 to 165° C. (preferably 125 to 160° C.)

The vapor stream from the evaporator 2 is continuously introduced to the distillation column 3 through the line 21. From the column top of the distillation column 3, a vapor as the overhead stream is continuously withdrawn to the line 24. From the column bottom of the distillation column 3, a bottom fraction is continuously withdrawn to the line 25. 3b denotes a reboiler. From the height position between the column top and the column bottom of the distillation column 3, the acetic acid stream (first acetic acid stream; liquid) as a side stream is continuously withdrawn through the line 27.

The vapor withdrawn from the column top of the distillation column 3 contains a larger amount of components having a lower boiling point (lower boiling point components) than that of acetic acid as compared with the bottom fraction and the side stream from the distillation column 3 and contains, for example, methyl iodide, hydrogen iodide, water, methyl acetate, dimethyl ether, methanol, acetaldehyde, and formic acid. This vapor also contains acetic acid. Such a vapor is continuously introduced to the condenser 3a through the line 24.

The condenser 3a separates the vapor from the distillation column 3 into a condensate portion and a gaseous portion by cooling and partial condensation. The condensate portion contains, for example, methyl iodide, hydrogen iodide, water, methyl acetate, acetic acid, dimethyl ether, methanol, acetaldehyde, and formic acid and is continuously introduced to the decanter 4 from the condenser 3a through the line 28. The condensate portion introduced to the decanter 4 is separated into an aqueous phase (upper phase) and an organic phase (methyl iodide phase; lower phase). The aqueous phase contains water and, for example, methyl iodide, hydrogen iodide, methyl acetate, acetic acid, dimethyl ether, methanol, acetaldehyde, and formic acid. The organic phase contains, for example, methyl iodide and, for example, hydrogen iodide, water, methyl acetate, acetic acid, dimethyl ether, methanol, acetaldehyde, and formic acid. In the present embodiment, a portion of the aqueous phase is refluxed to the distillation column 3 through the line 29, and another portion of the aqueous phase is introduced to the reaction vessel 1 through the lines 29, 30, and 23 and recycled. A portion of the organic phase is introduced to the reaction vessel 1 through the lines 31 and 23 and recycled. Another portion of the organic phase and/or a remaining portion of the aqueous phase is introduced to the acetaldehyde separation and removal system 9 through the lines 31 and 50 and/or the lines 30 and 51.

In the acetaldehyde separation and removal step using the acetaldehyde separation and removal system 9, acetaldehyde contained in the organic phase and/or the aqueous phase is separated and removed by a method known in the art, for example, distillation, extraction, or a combination thereof. The separated acetaldehyde is discharge to the outside of the apparatus through the line 53. The useful components (e.g., methyl iodide) contained in the organic phase and/or the aqueous phase are recycled to the reaction vessel 1 through the lines 52 and 23 and reused.

FIG. 2 is a schematic flow diagram showing one example of the acetaldehyde separation and removal system. According to this flow, in the case of treating, for example, the organic phase in the acetaldehyde separation and removal step, the organic phase is fed to a distillation column (first acetaldehyde removal column) 91 through a line 101 and separated by distillation into an overhead stream rich in acetaldehyde (line 102) and a residual liquid stream rich in methyl iodide (line 103). The overhead stream is condensed in a condenser 91a. A portion of the condensate is refluxed to the column top of the distillation column 91 (line 104), and the remaining portion of the condensate is fed to an extraction column 92 (line 105). The condensate fed to the extraction column 92 is subjected to extraction treatment with water introduced from a line 109. The extract obtained by the extraction treatment is fed to a distillation column (second acetaldehyde removal column) 93 through a line 107 and separated by distillation into an overhead stream rich in acetaldehyde (line 112) and a residual liquid stream rich in water (line 113). Then, the overhead stream rich in acetaldehyde is condensed in a condenser 93a. A portion of the condensate is refluxed to the column top of the distillation column 93 (line 114), and the remaining portion of the condensate is discharged to the outside of the system (line 115). The residual liquid stream rich in methyl iodide, which is a bottom fraction of the first acetaldehyde removal column 91, a raffinate rich in methyl iodide (line 108) obtained in the extraction column 92, and the residual liquid stream rich in water, which is a bottom fraction of the second acetaldehyde removal column 93 are recycled to the reaction vessel 1 through the lines 103, 111, and 113, respectively, or recycled to an appropriate area of the process and reused. For example, the raffinate rich in methyl iodide, obtained in the extraction column 92, can be recycled to the distillation column 91 through a line 110. The liquid from the line 113 is usually discharged to the outside as water discharge. A gas that has not been condensed in the condenser 91a or 93a (line 106 or 116) is subjected to absorption treatment in the scrubber system 8 or discarded.

According to the flow of FIG. 2, in the case of treating the aqueous phase in the acetaldehyde separation and removal step, for example, the aqueous phase is fed to the distillation column (first acetaldehyde removal column) 91 through the line 101 and separated by distillation into an overhead stream rich in acetaldehyde (line 102) and a residual liquid stream rich in water (line 103). The overhead stream is condensed in the condenser 91a. A portion of the condensate is refluxed to the column top of the distillation column 91 (line 104), and the remaining portion of the condensate is fed to the extraction column 92 (line 105). The condensate fed to the extraction column 92 is subjected to extraction treatment with water introduced from the line 109. The extract obtained by the extraction treatment is fed to the distillation column (second acetaldehyde removal column) 93 through the line 107 and separated by distillation into an overhead stream rich in acetaldehyde (line 112) and a residual liquid stream rich in water (line 113). Then, the overhead stream rich in acetaldehyde is condensed in the condenser 93a. A portion of the condensate is refluxed to the column top of the distillation column 93 (line 114), and the remaining portion of the condensate is discharged to the outside of the system (line 115). The residual liquid stream rich in water, which is a bottom fraction of the first acetaldehyde removal column 91, a raffinate rich in methyl iodide (line 108) obtained in the extraction column 92, and the residual liquid stream rich in water, which is a bottom fraction of the second acetaldehyde removal column 93 are recycled to the reaction vessel 1 through the lines 103, 111, and 113, respectively, or recycled to an appropriate area of the process and reused. For example, the raffinate rich in methyl iodide, obtained in the extraction column 92, can be recycled to the distillation column 91 through the line 110. The liquid from the line 113 is usually discharged to the outside as water discharge. A gas that has not been condensed in the condenser 91a or 93a (line 106 or 116) is subjected to absorption treatment in the scrubber system 8 or discarded.

The acetaldehyde derived from the process stream containing at least the water, the acetic acid (AC), the methyl iodide (MeI), and the acetaldehyde (AD) can also be separated and removed by use of extractive distillation, in addition to the method described above. For example, the organic phase and/or the aqueous phase (charging mixture) obtained by the separation of the process stream is fed to a distillation column (extractive distillation column). In addition, an extraction solvent (usually, water) is introduced to a concentration zone (e.g., space from the column top to the charging mixture feeding position) where methyl iodide and acetaldehyde in the distillation column are concentrated. A liquid (extract) dropped from the concentration zone is withdrawn as a side stream (side cut stream). This side stream is separated into an aqueous phase and an organic phase. The aqueous phase can be distilled to thereby discharge acetaldehyde to the outside of the system. In the case where a relatively large amount of water is present in the distillation column, the liquid dropped from the concentration zone may be withdrawn as a side stream without introducing the extraction solvent to the distillation column. For example, a unit (chimney tray, etc.) that can receive the liquid (extract) dropped from the concentration zone is disposed in this distillation column so that a liquid (extract) received by this unit can be withdrawn as a side stream. The extraction solvent introduction position is preferably superior to the charging mixture feeding position, more preferably near the column top. The side stream withdrawal position is preferably lower than the extraction solvent introduction position and higher than the charging mixture feeding position, in the height direction of the column. According to this method, acetaldehyde can be extracted with a high concentration from a concentrate of methyl iodide and the acetaldehyde using an extraction solvent (usually, water). In addition, the region between the extraction solvent introduction site and the side cut site is used as an extraction zone. Therefore, acetaldehyde can be efficiently extracted with a small amount of the extraction solvent. Therefore, for example, the number of plates in the distillation column can be drastically decreased as compared with a method of withdrawing an extract by extractive distillation from the column bottom of the distillation column (extractive distillation column). In addition, steam load can also be reduced. Furthermore, the ratio of methyl iodide to acetaldehyde (MeI/AD ratio) in a water extract can be decreased as compared with a method of combining the aldehyde removing distillation of FIG. 2 with water extraction using a small amount of an extraction solvent. Therefore, acetaldehyde can be removed under conditions that can suppress a loss of methyl iodide to the outside of the system. The acetaldehyde concentration in the side stream is much higher than the acetaldehyde concentration in the charging mixture and the bottom fraction (column bottom fraction). The ratio of acetaldehyde to methyl iodide in the side stream is larger than the ratio of acetaldehyde to methyl iodide in the charging mixture and the bottom fraction. The organic phase (methyl iodide phase) obtained by the separation of the side stream may be recycled to this distillation column. In this case, the recycle position of the organic phase obtained by the separation of the side stream is preferably lower than the side stream withdrawal position and preferably higher than the charging mixture feeding position, in the height direction of the column. A solvent miscible with the components (e.g., methyl acetate) constituting the organic phase obtained by the separation of the process stream may be introduced to this distillation column (extractive distillation column). Examples of the miscible solvent include acetic acid and ethyl acetate. The miscible solvent introduction position is preferably lower than the side stream withdrawal position and preferably higher than the charging mixture feeding position, in the height direction of the column. Also, the miscible solvent introduction position is preferably inferior to a recycle position in the case where the organic phase obtained by the separation of the side stream is recycled to this distillation column. The organic phase obtained by the separation of the side stream is recycled to the distillation column, or the miscible solvent is introduced to the distillation column, whereby the methyl acetate concentration in the extract withdrawn as the side stream can be decreased, and the methyl acetate concentration in the aqueous phase obtained by the separation of the extract can be lowered. Hence, the contamination of the aqueous phase with methyl iodide can be suppressed.

The theoretical number of plates of the distillation column (extractive distillation column) is, for example, 1 to 100, preferably 2 to 50, further preferably 3 to 30, particularly preferably 5 to 20. Acetaldehyde can be efficiently separated and removed by a smaller number of plates than 80 to 100 plates in a distillation column or an extractive distillation column for use in conventional acetaldehyde removal. The mass ratio between the flow rate of the extraction solvent and the flow rate of the charging mixture (the organic phase and/or the aqueous phase obtained by the separation of the process stream) (former/latter) may be selected from the range of 0.0001/100 to 100/100 and is usually 0.0001/100 to 20/100, preferably 0.001/100 to 10/100, more preferably 0.01/100 to 8/100, further preferably 0.1/100 to 5/100. The column top temperature of the distillation column (extractive distillation column) is, for example, 15 to 120° C., preferably 20 to 90° C., more preferably 20 to 80° C., further preferably 25 to 70° C. The column top pressure is, on the order of, for example, 0.1 to 0.5 MPa in terms of absolute pressure. Other conditions for the distillation column (extractive distillation column) may be the same as those for a distillation column or an extractive distillation column for use in conventional acetaldehyde removal.

FIG. 3 is a schematic flow diagram showing another example of the acetaldehyde separation and removal system using the extractive distillation described above. In this example, the organic phase and/or the aqueous phase (charging mixture) obtained by the separation of the process stream is fed to a middle part (position between the column top and the column bottom) of a distillation column 94 through a feed line 201, while water is introduced thereto from near the column top through a line 202 so that extractive distillation is performed in the distillation column 94 (extractive distillation column). A chimney tray 200 for receiving a liquid (extract) dropped from a concentration zone where methyl iodide and acetaldehyde in the column are concentrated is disposed superior to the charging mixture feeding position of the distillation column 94. In this extractive distillation, preferably the whole amount, of the liquid on the chimney tray 200 is withdrawn, introduced to a decanter 95 through a line 208, and separated. The aqueous phase (containing acetaldehyde) in the decanter 95 is introduced to a cooler 95a through a line 212 and cooled so that methyl iodide dissolved in the aqueous phase is separated into 2 phases in a decanter 96. The aqueous phase in the decanter 96 is fed to a distillation column 97 (acetaldehyde removal column) through a line 216 and distilled. The vapor at the column top is led to a condenser 97a through a line 217 and condensed. A portion of the condensate (mainly, acetaldehyde and methyl iodide) is refluxed to the column top of the distillation column 97, and the remaining portion is discarded or fed to a distillation column 98 (extractive distillation column) through a line 220. Water is introduced thereto from near the column top of the distillation column 98 through a line 222, followed by extractive distillation. The vapor at the column top is led to a condenser 98a through a line 223 and condensed. A portion of the condensate (mainly, methyl iodide) is refluxed to the column top, and the remaining portion is recycled to the reaction system through a line 226, but may be discharged to the outside of the system. Preferably the whole amount, of the organic phase (methyl iodide phase) in the decanter 95 is recycled to below the position of the chimney tray 200 of the distillation column 94 through lines 209 and 210. A portion of the aqueous phase of the decanter 95 and the organic phase of the decanter 96 are recycled to the distillation column 94 through lines 213 and 210 and lines 214 and 210, respectively, but may not be recycled. A portion of the aqueous phase of the decanter 95 may be utilized as an extraction solvent (water) in the distillation column 94. A portion of the aqueous phase of the decanter 96 may be recycled to the distillation column 94 through the line 210. In some cases (e.g., the case where methyl acetate is contained in the charging mixture), a solvent (acetic acid, ethyl acetate, etc.) miscible with the components (e.g., methyl acetate) constituting the organic phase obtained by the separation of the process stream may be fed to the distillation column 94 through a line 215 to thereby improve distillation efficiency. The feeding position of the miscible solvent to the distillation column 94 is superior to the charging mixture feeding portion (junction of the line 201) and inferior to the junction of the recycle line 210. A bottom fraction of the distillation column 94 is recycled to the reaction system. A vapor at the column top of the distillation column 94 is led to a condenser 94a through a line 203 and condensed. The condensate is separated in a decanter 99. The organic phase is refluxed to the column top of the distillation column 94 through a line 206, while the aqueous phase is led to the decanter 95 through a line 207. A bottom fraction (water is a main component) of the distillation column 97 and a bottom fraction (water containing a small amount of acetaldehyde) of the distillation column 98 (extractive distillation column) are discharged to the outside of the system through lines 218 and 224, respectively, or recycled to the reaction system. A gas that has not been condensed in the condenser 94a, 97a, or 98a (line 211, 221, or 227) is subjected to absorption treatment in the scrubber system 8, or discarded.

FIG. 4 is a schematic flow diagram showing a further alternative example of the acetaldehyde separation and removal system using the extractive distillation described above. In this example, a condensate of a vapor from the column top of the distillation column 94 is led to a hold tank 100, and the whole amount thereof is refluxed to the column top of the distillation column 94 through the line 206. The other points are the same as in the example of FIG. 3.

FIG. 5 is a schematic flow diagram showing a further alternative example of the acetaldehyde separation and removal system using the extractive distillation described above. In this example, the whole amount of a liquid on the chimney tray 200 is withdrawn, directly introduced to the cooler 95a through the line 208 without the medium of the decanter 95, cooled, and fed to the decanter 96. The other points are the same as in the example of FIG. 4.

In FIG. 1 described above, the gaseous portion generated in the condenser 3a contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid and is fed to the scrubber system 8 from the condenser 3a through the lines 32 and 15. For example, methyl iodide, hydrogen iodide, water, methyl acetate, acetic acid, dimethyl ether, methanol, acetaldehyde, and formic acid in the gaseous portion that has entered the scrubber system 8 are absorbed to an absorbing liquid in the scrubber system 8. The hydrogen iodide generates methyl iodide through reaction with methanol or methyl acetate in the absorbing liquid. Then, a liquid portion containing useful components such as the methyl iodide is recycled to the reaction vessel 1 from the scrubber system 8 through the recycle lines 48 and 23 and reused.

The bottom fraction withdrawn from the column bottom of the distillation column 3 contains a larger amount of components having a higher boiling point (higher boiling point components) than that of acetic acid as compared with the overhead stream and the side stream from the distillation column 3 and contains, for example, propionic acid, and the entrained catalyst and co-catalyst mentioned above. This bottom fraction also contains, for example, acetic acid, methyl iodide, methyl acetate, and water. In the present embodiment, a portion of such a bottom fraction is continuously introduced to the evaporator 2 through the lines 25 and 26 and recycled, and another portion of the bottom fraction is continuously introduced to the reaction vessel 1 through the lines 25 and 23 and recycled.

The first acetic acid stream continuously withdrawn as a side stream from the distillation column 3 is more enriched with acetic acid than the vapor stream continuously introduced to the distillation column 3. Specifically, the acetic acid concentration of the first acetic acid stream is higher than the acetic acid concentration of the vapor stream. The acetic acid concentration of the first acetic acid stream is, for example, 90 to 99.9% by mass, preferably 93 to 99% by mass. Also, the first acetic acid stream may contain, in addition to acetic acid, for example, methyl iodide, hydrogen iodide, water, methyl acetate, dimethyl ether, methanol, acetaldehyde, formic acid, and propionic acid. The first acetic acid stream has a methyl iodide concentration of, for example, not more than 8% by mass (0.1 to 8% by mass), preferably 0.2 to 5% by mass, a water concentration of, for example, not more than 8% by mass (0.1 to 8% by mass), preferably 0.2 to 5% by mass, and a methyl acetate concentration of, for example, not more than 8% by mass (0.1 to 8% by mass), preferably 0.2 to 5% by mass. The connection position of the line 27 to the distillation column 3 may be, as shown in the drawing, higher than the connection position of the line 21 to the distillation column 3 in the height direction of the distillation column 3, but may be lower than the connection position of the line 21 to the distillation column 3 or may be the same as the connection position of the line 21 to the distillation column 3. The first acetic acid stream from the distillation column 3 is continuously introduced at a predetermined flow rate to the next distillation column 5 through the line 27. The first acetic acid stream withdrawn as a side stream from the distillation column 3, column bottom fraction of the distillation column 3, or condensate of the vapor in the column bottom of the distillation column 3 may be directly and continuously introduced into the distillation column 6 described below without using the distillation column 5 (dehydration step).

To the first acetic acid stream flowing through the line 27, potassium hydroxide can be fed or added through the line 55 (potassium hydroxide introduction line). The potassium hydroxide can be fed or added, for example, as a solution such as an aqueous solution. Hydrogen iodide in the first acetic acid stream can be decreased by the feed or addition of potassium hydroxide to the first acetic acid stream. Specifically, the hydrogen iodide reacts with the potassium hydroxide to form potassium iodide and water. This can reduce the corrosion of an apparatus such as a distillation column ascribable to hydrogen iodide. In this process, the potassium hydroxide can be fed or added to an appropriate site where hydrogen iodide is present. The potassium hydroxide added during the process also reacts with acetic acid to form potassium acetate.

The distillation column 5 is a unit for performing the second distillation step and serves as the so-called dehydration column in the present embodiment. The second distillation step is a step for further purifying acetic acid by the distillation treatment of the first acetic acid stream continuously introduced to the distillation column 5. In the distillation column 5, it is preferred that, as specified by the present invention, the first acetic acid stream fed through the line 27 should be distilled under a condition involving a column bottom temperature of not more than 165° C. to obtain purified acetic acid. The distillation column 5 consists of, for example, a distillation column such as a plate column or a packed column. In the case of adopting a plate column as the distillation column 5, the theoretical number of plates thereof is, for example, 5 to 50, and the reflux ratio is, for example, 0.2 to 3000 according to the theoretical number of plates. In the inside of the distillation column 5 in the second distillation step, it is preferred that the column top pressure and the column bottom pressure should be set according to the composition of the column bottom fraction such that the column bottom temperature is not more than 165° C. The column top pressure is, for example, 0.10 to 0.28 MPaG, preferably 0.15 to 0.23 MPaG, further preferably 0.17 to 0.21 MPaG. The column bottom pressure is higher than the column top pressure and is, for example, 0.13 to 0.31 MPaG, preferably 0.18 to 0.26 MPaG, further preferably 0.20 to 0.24 MPaG. In the inside of the distillation column 5 in the second distillation step, the column top temperature is, for example, a temperature of higher than the boiling point of water and lower than the boiling point of acetic acid at the set column top pressure and is set to 110 to 160° C., and the column bottom temperature is, for example, a temperature of not less than the boiling point of acetic acid at the set column bottom pressure and is set to 120 to 165° C. (preferably 125 to 160° C., further preferably 130 to 155° C.)

A vapor as an overhead stream is continuously withdrawn to the line 33 from the column top of the distillation column 5. A bottom fraction is continuously withdrawn to the line 34 from the column bottom of the distillation column 5. 5b denotes a reboiler. A side stream (liquid or gas) may be continuously withdrawn to the line 34 from the height position between the column top and the column bottom of the distillation column 5.

The vapor withdrawn from the column top of the distillation column 5 contains a larger amount of components having a lower boiling point (lower boiling point components) than that of acetic acid as compared with the bottom fraction from the distillation column 5 and contains, for example, methyl iodide, hydrogen iodide, water, methyl acetate, acetic acid, dimethyl ether, methanol, acetaldehyde, and formic acid. Such a vapor is continuously introduced to the condenser 5a through the line 33.

The condenser 5a separates the vapor from the distillation column 5 into a condensate portion and a gaseous portion by cooling and partial condensation. The condensate portion contains, for example, water and acetic acid. A portion of the condensate portion is continuously refluxed to the distillation column 5 from the condenser 5a through the line 35. Another portion of the condensate portion is continuously introduced to the reaction vessel 1 from the condenser 5a through the lines 35, 36, and 23 and recycled. The gaseous portion generated in the condenser 5a contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid and is fed to the scrubber system 8 from the condenser 5a through the lines 37 and 15. Hydrogen iodide in the gaseous portion that has entered the scrubber system 8 is absorbed to an absorbing liquid in the scrubber system 8. Methyl iodide is generated through the reaction of the hydrogen iodide with methanol or methyl acetate in the absorbing liquid. Then, a liquid portion containing useful components such as the methyl iodide is recycled to the reaction vessel 1 from the scrubber system 8 through the recycle lines 48 and 23 and reused.

The bottom fraction (or the side stream) withdrawn from the column bottom of the distillation column 5 contains a larger amount of components having a higher boiling point (higher boiling point components) than that of acetic acid as compared with the overhead stream from the distillation column 5 and contains, for example, propionic acid, potassium acetate (in the case of feeding potassium hydroxide to the line 27, etc.), and the entrained catalyst and co-catalyst mentioned above. This bottom fraction may also contain acetic acid. Such a bottom fraction is continuously introduced in the form of the second acetic acid stream to the next distillation column 6 through the line 34.

The second acetic acid stream is more enriched with acetic acid than the first acetic acid stream continuously introduced to the distillation column 5. Specifically, the acetic acid concentration of the second acetic acid stream is higher than the acetic acid concentration of the first acetic acid stream. The acetic acid concentration of the second acetic acid stream is, for example, 99.1 to 99.99% by mass as long as being higher than the acetic acid concentration of the first acetic acid stream. Also, the second acetic acid stream may contain, as described above, in addition to acetic acid, for example, propionic acid and hydrogen iodide. In the present embodiment, in the case of withdrawing a side stream, the withdrawal position of the side stream from the distillation column 5 is lower than the introduction position of the first acetic acid stream to the distillation column 5 in the height direction of the distillation column 5.

To the second acetic acid stream flowing through the line 34, potassium hydroxide can be fed or added through the line 56 (potassium hydroxide introduction line). The potassium hydroxide can be fed or added, for example, as a solution such as an aqueous solution. Hydrogen iodide in the second acetic acid stream can be decreased by the feed or addition of potassium hydroxide to the second acetic acid stream. Specifically, the hydrogen iodide reacts with the potassium hydroxide to form potassium iodide and water. This can reduce the corrosion of an apparatus such as a distillation column ascribable to hydrogen iodide.

The distillation column 6 is a unit for performing the third distillation step and serves as the so-called higher boiling point component removal column in the present embodiment. The third distillation step is a step for further purifying acetic acid by the purification treatment of the second acetic acid stream continuously introduced to the distillation column 6. In the distillation column 6, it is preferred that, as specified by the present invention, the second acetic acid stream fed through the line 34 should be distilled under a condition involving a column bottom temperature of not more than 165° C. to obtain purified acetic acid. The distillation column 6 consists of, for example, a distillation column such as a plate column or a packed column. In the case of adopting a plate column as the distillation column 6, the theoretical number of plates thereof is, for example, 5 to 50, and the reflux ratio is, for example, 0.2 to 3000 according to the theoretical number of plates. In the inside of the distillation column 6 in the third distillation step, it is preferred that the column top pressure and the column bottom pressure should be set according to the composition of the column bottom fraction such that the column bottom temperature is not more than 165° C. The column top pressure is, for example, 0.005 to 0.24 MPaG, preferably 0.01 to 0.22 MPaG, further preferably 0.02 to 0.20 MPaG, particularly preferably 0.04 to 0.19 MPaG. The column bottom pressure is higher than the column top pressure and is, for example, not less than 0.01 MPaG and less than 0.255 MPaG, preferably 0.02 to 0.24 MPaG, further preferably 0.03 to 0.23 MPaG, particularly preferably 0.05 to 0.21 MPaG. In the inside of the distillation column 6 in the third distillation step, the column top temperature is, for example, a temperature of higher than the boiling point of water and lower than the boiling point of acetic acid at the set column top pressure and is set to 50 to 160° C., and the column bottom temperature is, for example, a temperature of higher than the boiling point of acetic acid at the set column bottom pressure and is set to 70 to 165° C. (preferably 120 to 160° C., further preferably 130 to 155° C.)

A vapor as an overhead stream is continuously withdrawn to the line 38 from the column top of the distillation column 6. A bottom fraction is continuously withdrawn to the line 39 from the column bottom of the distillation column 6. 6b denotes a reboiler. A side stream (liquid or gas) is continuously withdrawn to the line 46 from the height position between the column top and the column bottom of the distillation column 6. The connection position of the line 46 to the distillation column 6 may be, as shown in the drawing, higher than the connection position of the line 34 to the distillation column 6 in the height direction of the distillation column 6, but may be lower than the connection position of the line 34 to the distillation column 6 or may be the same as the connection position of the line 34 to the distillation column 6.

The vapor withdrawn from the column top of the distillation column 6 contains a larger amount of components having a lower boiling point (lower boiling point components) than that of acetic acid as compared with the bottom fraction from the distillation column 6 and contains, in addition to acetic acid, for example, methyl iodide, hydrogen iodide, water, methyl acetate, dimethyl ether, methanol, and formic acid. Such a vapor is continuously introduced to the condenser 6a through the line 38.

The condenser 6a separates the vapor from the distillation column 6 into a condensate portion and a gaseous portion by cooling and partial condensation. The condensate portion contains, in addition to acetic acid, for example, methyl iodide, hydrogen iodide, water, methyl acetate, dimethyl ether, methanol, and formic acid. At least a portion of the condensate portion is continuously refluxed to the distillation column 6 from the condenser 6a through the line 40. A portion (distillate) of the condensate portion may be recycled to the first acetic acid stream in the line 27 before introduction to the distillation column 5 from the condenser 6a through the lines 40, 41, and 42. Together with this or instead of this, a portion (distillate) of the condensate portion may be recycled to the vapor stream in the line 21 before introduction to the distillation column 3 from the condenser 6a through the lines 40, 41, and 43. Also, a portion (distillate) of the condensate portion may be recycled to the reaction vessel 1 from the condenser 6a through the lines 40, 44, and 23. Furthermore, as mentioned above, a portion of the distillate from the condenser 6a may be fed to the scrubber system 8 and used as an absorbing liquid in this system. In the scrubber system 8, a gaseous portion after absorption of a useful portion is discharged to the outside of the apparatus. Then, a liquid portion containing the useful components is introduced or recycled to the reaction vessel 1 from the scrubber system 8 through the recycle lines 48 and 23 and reused. In addition, a portion of the distillate from the condenser 6a may be led to various pumps (not shown) operated in the apparatus, through lines (not shown) and used as sealing solutions in these pumps. In addition, a portion of the distillate from the condenser 6a may be steadily withdrawn to the outside of the apparatus through a withdrawal line attached to the line 40, or may be non-steadily withdrawn to the outside of the apparatus when needed. In the case where a portion (distillate) of the condensate portion is removed from the distillation treatment system in the distillation column 6, the amount of the distillate (ratio of the distillate) is, for example, 0.01 to 30% by mass, preferably 0.1 to 10% by mass, more preferably 0.3 to 5% by mass, more preferably 0.5 to 3% by mass, of the condensate generated in the condenser 6a. On the other hand, the gaseous portion generated in the condenser 6a contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid and is fed to the scrubber system 8 from the condenser 6a through the lines 45 and 15.

The bottom fraction withdrawn from the column bottom of the distillation column 6 through the line 39 contains a larger amount of components having a higher boiling point (higher boiling point components) than that of acetic acid as compared with the overhead stream from the distillation column 6 and contains, for example, acetate salt such as potassium acetate (in the case of feeding an alkali such as potassium hydroxide to the line 34, etc.), acetic anhydride, and propionic acid. Also, the bottom fraction withdrawn from the column bottom of the distillation column 6 through the line 39 also contains, for example, a corroded metal such as a metal formed at and released from the inside wall of a member constituting this acetic acid production apparatus, and a compound of iodine derived from corrosive iodine and the corroded metal, etc. In the present embodiment, such a bottom fraction is discharged to the outside of the acetic acid production apparatus.

In the present invention, lower acetate, acetic anhydride, and propionic acid concentrations in the column bottom fraction of the distillation column 6 are more preferred from the viewpoint of suppressing the corrosion of the distillation column. The acetate salt concentration in the column bottom fraction of the distillation column 6 is, for example, 1 ppm by mass to 34% by mass, preferably 100 ppm by mass to 25% by mass, further preferably 0.1 to 20% by mass (e.g., 1 to 15% by mass). The acetic anhydride concentration in the column bottom fraction of the distillation column 6 is, for example, 1 ppm by mass to 91% by mass, preferably 10 ppm by mass to 74% by mass, more preferably 100 ppm by mass to 44% by mass, further preferably 0.1 to 20% by mass, particularly preferably 0.2 to 10% by mass (e.g., 0.5 to 5% by mass). The propionic acid concentration in the column bottom fraction of the distillation column 6 is, for example, 100 ppm by mass to 91% by mass, preferably 0.1 to 75% by mass, more preferably 0.3 to 55% by mass, further preferably 0.5 to 29% by mass, particularly preferably 1 to 15% by mass. The acetate salt concentration in the column bottom fraction of the distillation column 6 can be lowered, for example, by decreasing the amount of an alkali added for use in the neutralization of the hydrogen iodide. Also, the acetic anhydride concentration in the column bottom fraction of the distillation column 6 can be lowered, for example, by hydrolyzing the acetic anhydride by the addition of water into piping or an apparatus positioned upstream of the distillation column 6, or into the distillation column 6. The propionic acid concentration in the column bottom fraction of the distillation column 6 can be lowered by, for example, reduction in the production of the by-product propionic acid in a reaction vessel by changing reaction conditions, separation and removal of acetaldehyde responsible for the production of the by-product propionic acid from a process solution during recycle of a portion of the process solution to the reaction system, followed by recycle to the reaction system, or disposition of a distillation column or an evaporator (propionic acid removal column) for propionic acid separation and removal upstream of the distillation column 6.

The side stream continuously withdrawn to the line 46 from the distillation column 6 is continuously introduced as a third acetic acid stream to the next ion exchange resin column 7. This third acetic acid stream is more enriched with acetic acid than the second acetic acid stream continuously introduced to the distillation column 6. Specifically, the acetic acid concentration of the third acetic acid stream is higher than the acetic acid concentration of the second acetic acid stream. The acetic acid concentration of the third acetic acid stream is, for example, 99.8 to 99.999% by mass as long as being higher than the acetic acid concentration of the second acetic acid stream. In the present embodiment, the withdrawal position of the side stream from the distillation column 6 is higher than the introduction position of the second acetic acid stream to the distillation column 6 in the height direction of the distillation column 6. In another embodiment, the withdrawal position of the side stream from the distillation column 6 is the same as or lower than the introduction position of the second acetic acid stream to the distillation column 6 in the height direction of the distillation column 6. A simple distillator (evaporator) may be used in place of the distillation column 6. Also, the distillation column 6 can be omitted as long as the removal of impurities in the distillation column 5 is adequately performed.

The ion exchange resin column 7 is a purification unit for performing the adsorptive removal step. This adsorptive removal step is a step for further purifying acetic acid by the adsorptive removal of, mainly, alkyl iodides (hexyl iodide, decyl iodide, etc.) contained in a very small amount in the third acetic acid stream continuously introduced to the ion exchange resin column 7. In the ion exchange resin column 7, an ion exchange resin having the ability to adsorb alkyl iodides is packed in the column to establish an ion exchange resin bed. Examples of such an ion exchange resin can include cation exchange resins in which a portion of leaving protons in an exchange group such as a sulfonic acid group, a carboxyl group, or a phosphonic acid group is substituted by a metal such as silver or copper. In the adsorptive removal step, for example, the third acetic acid stream (liquid) flows through the inside of the ion exchange resin column 7 packed with such an ion exchange resin, and in the course of this flow, impurities such as the alkyl iodides in the third acetic acid stream are adsorbed to the ion exchange resin and removed from the third acetic acid stream. In the ion exchange resin column 7 in the adsorptive removal step, the internal temperature is, for example, 18 to 100° C., and the rate of the acetic acid stream [the throughput of acetic acid per m³ resin volume (m/h)] is, for example, 3 to 15 m/h·m³ (resin volume).

A fourth acetic acid stream is continuously led to the line 47 from the lower end of the ion exchange resin column 7. The acetic acid concentration of the fourth acetic acid stream is higher than the acetic acid concentration of the third acetic acid stream. Specifically, the fourth acetic acid stream is more enriched with acetic acid than the third acetic acid stream continuously introduced to the ion exchange resin column 7. The acetic acid concentration of the fourth acetic acid stream is, for example, 99.9 to 99.999% by mass or not less than this range as long as being higher than the acetic acid concentration of the third acetic acid stream. In this production method, this fourth acetic acid stream can be retained in a product tank (not shown).

In this acetic acid production apparatus, a so-called product column or finishing column which is a distillation column may be disposed as a purification unit for further purifying the fourth acetic acid stream from the ion exchange resin column 7. In such a product column as well, it is preferred that, as specified by the present invention, the fourth acetic acid stream fed through the line 47 should be distilled under a condition involving a column bottom temperature of not more than 165° C. to obtain purified acetic acid. In the case where such a product column is disposed, the product column consists of, for example, a distillation column such as a plate column or a packed column. In the case of adopting a plate column as the product column, the theoretical number of plates thereof is, for example, 5 to 50, and the reflux ratio is, for example, 0.5 to 3000 according to the theoretical number of plates. In the inside of the product column in the purification step, it is preferred that the column top pressure and the column bottom pressure should be set according to the composition of the column bottom fraction such that the column bottom temperature is not more than 165° C. The column top pressure is, for example, 0.005 to 0.24 MPaG, preferably 0.01 to 0.22 MPaG, further preferably 0.02 to 0.20 MPaG, particularly preferably 0.04 to 0.19 MPaG. The column bottom pressure is higher than the column top pressure and is, for example, not less than 0.01 MPaG and less than 0.255 MPaG, preferably 0.02 to 0.24 MPaG, further preferably 0.03 to 0.23 MPaG, particularly preferably 0.05 to 0.21 MPaG. In the inside of the product column in the purification step, the column top temperature is, for example, a temperature of higher than the boiling point of water and lower than the boiling point of acetic acid at the set column top pressure and is set to 50 to 160° C., and the column bottom temperature is, for example, a temperature of higher than the boiling point of acetic acid at the set column bottom pressure and is set to 70 to 165° C. (preferably 120 to 160° C., further preferably 130 to 155° C.). A simple distillator (evaporator) may be used in place of the product column or the finishing column.

In the case of disposing the product column, the whole or a portion of the fourth acetic acid stream (liquid) from the ion exchange resin column 7 is continuously introduced to the product column. A vapor as an overhead stream containing a very small amount of lower boiling point components (e.g., methyl iodide, water, methyl acetate, dimethyl ether, crotonaldehyde, acetaldehyde, and formic acid) is continuously withdrawn from the column top of such a product column. This vapor is separated into a condensate portion and a gaseous portion in a predetermined condenser. A portion of the condensate portion is continuously refluxed to the product column, and another portion of the condensate portion may be recycled to the reaction vessel 1 or discarded to the outside of the system, or both. The gaseous portion is fed to the scrubber system 8. A bottom fraction containing a very small amount of higher boiling point components is continuously withdrawn from the column bottom of the product column. This bottom fraction is recycled to, for example, the second acetic acid stream in the line 34 before introduction to the distillation column 6. A side stream (liquid) is continuously withdrawn as a fifth acetic acid stream from the height position between the column top and the column bottom of the product column. The withdrawal position of the side stream from the product column is lower than, for example, the introduction position of the fourth acetic acid stream to the product column in the height direction of the product column. The fifth acetic acid stream is more enriched with acetic acid than the fourth acetic acid stream continuously introduced to the product column. Specifically, the acetic acid concentration of the fifth acetic acid stream is higher than the acetic acid concentration of the fourth acetic acid stream. The acetic acid concentration of the fifth acetic acid stream is, for example, 99.9 to 99.999% by mass or not less than this range as long as being higher than the acetic acid concentration of the fourth acetic acid stream. This fifth acetic acid stream is retained in, for example, a product tank (not shown). The ion exchange resin column 7 may be placed downstream of the product column instead of (or in addition to) its placement downstream of the distillation column 6 to treat the acetic acid stream from the product column.

In the present invention, lower acetate, acetic anhydride, and propionic acid concentrations in the column bottom fraction of the product column are more preferred from the viewpoint of suppressing the corrosion of the distillation column. The acetate salt concentration in the column bottom fraction of the product column is, for example, 0.1 ppb by mass to 1% by mass, preferably 1 ppb by mass to 0.1% by mass, further preferably 10 ppb by mass to 0.01% by mass (e.g., 100 ppb by mass to 0.001% by mass). The acetic anhydride concentration in the column bottom fraction of the product column is, for example, 0.1 ppm by mass to 60% by mass, preferably 1 ppm by mass to 10% by mass, further preferably 10 ppm by mass to 2% by mass (e.g., 50 ppm by mass to 0.5% by mass) or may be 0.2 to 10% by mass (e.g., 0.5 to 5% by mass). The propionic acid concentration in the column bottom fraction of the product column is, for example, 1 ppm by mass to 10% by mass, preferably 10 ppm by mass to 5% by mass, further preferably 50 ppm by mass to 1% by mass (e.g., 100 ppm by mass to 0.1% by mass). The acetate salt concentration in the column bottom fraction of the product column can be lowered, for example, by decreasing the amount of an alkali added for use in the neutralization of the hydrogen iodide. Also, the acetic anhydride concentration in the column bottom fraction of the product column can be lowered, for example, by hydrolyzing the acetic anhydride by the addition of water into piping or an apparatus positioned upstream of the product column, or into the product column. The propionic acid concentration in the column bottom fraction of the product column can be lowered by, for example, reduction in the production of the by-product propionic acid in a reaction vessel by changing reaction conditions, separation and removal of acetaldehyde responsible for the production of the by-product propionic acid from a process solution during recycle of a portion of the process solution to the reaction system, followed by recycle to the reaction system, or disposition of a distillation column or an evaporator (propionic acid removal column) for propionic acid separation and removal upstream of the product column.

In the embodiments described above, among the distillation column 5, the distillation column 6, and the product column, for example, the column bottom temperature of the distillation column 5 may be set to not more than 165° C. (e.g., less than 165° C.). The column bottom temperature of the distillation column 6 may be set to not more than 165° C. (e.g., less than 165° C.). The column bottom temperature of the product column may be set to not more than 165° C. (e.g., less than 165° C.). The column bottom temperatures of the distillation column 5 and the distillation column 6 may be set to not more than 165° C. (e.g., less than 165° C.). The column bottom temperatures of the distillation column 6 and the product column may be set to not more than 165° C. (e.g., less than 165° C.). The column bottom temperatures of all the three distillation columns, i.e., the distillation column 5, the distillation column 6, and the product column, may be set to not more than 165° C. (e.g., less than 165° C.). Each of their column bottom temperatures is preferably not more than 160° C., further preferably not more than 155° C., particularly preferably not more than 150° C. (e.g., not more than 140° C.). As described above, the distillation column 6 or the product column (particularly the latter) may be omitted.

EXAMPLES

Hereinafter, the present invention will be described in more detail with reference to Examples. However, the present invention is not intended to be limited by these Examples.

Comparative Example 1

459 g of propionic acid and 46 g of acetic acid were placed in a 1000 ml zirconium autoclave, and a test piece (size: 36 mm×25 mm×2.5 mm) of zirconium (Zr), a nickel-based alloy Hastelloy B2 (manufactured by Oda Koki Co., Ltd., "HB2"), a nickel-based alloy Hastelloy C (manufactured by Oda Koki Co., Ltd., "HC276"), or stainless steel SUS316 (manufactured by Umetoku Inc., "SUS316") as each material was placed in the autoclave, which was then covered with a lid. The liquid in the autoclave was bubbled with nitrogen to purge oxygen dissolved in the liquid. Then, the operation of increasing the atmospheric pressure with nitrogen to 1 MPaG, which was then reduced to the atmospheric pressure was carried out three times. Then, nitrogen gas was introduced thereto to 4 MPaG, and the pressure was discharged until atmospheric pressure. Then, the autoclave was heated in an oil bath such that the liquid temperature in the autoclave was 165° C. The static pressure after the heating was changed to 131 kPaG. After a lapse of 500 hours under static conditions, the autoclave was cooled to room temperature, and the pressure was discharged. Then, the test piece was taken out thereof, and its corrosion rate was calculated by weight measurement. The presence or absence of local corrosion was determined by appearance inspection. The feed composition, conditions for the corrosion test, and results thereof are shown in Tables 1 and 2. "G" in the unit of pressure represents gauge pressure.

Comparative Example 2

A corrosion test was conducted in the same way as in Comparative Example 1 except that the feed composition was changed to 100% of acetic acid. The feed composition, conditions for the corrosion test, and results thereof are shown in Tables 1 and 2.

Examples 1 to 15

A corrosion test was conducted in the same way as in Comparative Example 1 except that the feed composition and the temperature were changed. The feed composition, conditions for the corrosion test, and results thereof are shown in Tables 1 and 2.

In all of Comparative Examples and Examples, partial corrosion or the like did not occur in the test pieces, and only overall uniform corrosion was found. In Table 2, the unit "mm/Y" means the corrosion rate (amount of decrease in thickness) of each test piece per year converted to mm.

TABLE 1

|  | Potassium acetate wt % | Acetic anhydride wt % | Propionic acid wt % | Acetic acid wt % | Temperature ° C. | Pressure kPaG |
| --- | --- | --- | --- | --- | --- | --- |
| Comparative Example 1 | 0 | 0 | 92.1 | 7.9 | 165.2 | 131 |
| Comparative Example 2 | 0 | 0 | 0 | 100 | 165.1 | 255 |
| Example 1 | 0 | 0 | 91.8 | 8.2 | 160.5 | 93 |
| Example 2 | 0 | 0 | 0 | 100 | 160.2 | 217 |
| Example 3 | 34.1 | 0 | 0 | 65.9 | 155.1 | 91 |
| Example 4 | 0 | 91.1 | 0 | 8.9 | 154.8 | 89 |
| Example 5 | 0 | 0 | 75.3 | 24.7 | 155.3 | 90 |
| Example 6 | 0 | 0 | 0 | 100 | 155.1 | 181 |
| Example 7 | 23.2 | 0 | 0 | 76.8 | 150.5 | 92 |
| Example 8 | 0 | 74.3 | 0 | 25.7 | 150.3 | 90 |
| Example 9 | 0 | 0 | 55.4 | 44.6 | 150.9 | 93 |
| Example 10 | 0 | 0 | 0 | 100 | 150 | 147 |
| Example 11 | 12.6 | 0 | 0 | 87.4 | 144.3 | 88 |
| Example 12 | 0 | 44.8 | 0 | 55.2 | 144.7 | 90 |
| Example 13 | 0 | 0 | 29 | 71 | 144.6 | 91 |
| Example 14 | 0 | 0 | 0 | 100 | 145.2 | 117 |
| Example 15 | 0 | 0 | 0 | 100 | 140.1 | 90 |

TABLE 2

| | Results of corrosion test | | | |
|---|---|---|---|---|
| | Zr mm/y | HB2 mm/y | HC276 mm/y | SUS316 mm/y |
| Comparative Example 1 | 0.000 | 0.05 | 0.12 | 0.22 |
| Comparative Example 2 | 0.000 | 0.05 | 0.12 | 0.21 |
| Example 1 | 0.000 | 0.04 | 0.082 | 0.17 |
| Example 2 | 0.000 | 0.04 | 0.081 | 0.15 |
| Example 3 | 0.000 | 0.028 | 0.049 | 0.105 |
| Example 4 | 0.000 | 0.03 | 0.05 | 0.113 |
| Example 5 | 0.000 | 0.029 | 0.051 | 0.095 |
| Example 6 | 0.000 | 0.027 | 0.048 | 0.092 |
| Example 7 | 0.000 | 0.020 | 0.030 | 0.049 |
| Example 8 | 0.000 | 0.020 | 0.034 | 0.053 |
| Example 9 | 0.000 | 0.021 | 0.033 | 0.051 |
| Example 10 | 0.000 | 0.019 | 0.03 | 0.030 |
| Example 11 | 0.000 | 0.009 | 0.018 | 0.031 |
| Example 12 | 0.000 | 0.008 | 0.016 | 0.029 |
| Example 13 | 0.000 | 0.008 | 0.015 | 0.023 |
| Example 14 | 0.000 | 0.007 | 0.013 | 0.025 |
| Example 15 | 0.000 | 0.000 | 0.005 | 0.011 |

[Discussion on Results]

Through Comparative Examples and Examples, zirconium (Zr) exhibited complete corrosion resistance in all of the samples.

From the results of Comparative Examples 1 and 2, the corrosion rate was a level at which only a durable material (Zr, etc.) equal to or superior to HB2 could be used at a temperature of more than the temperature 165° C. In Examples 1 to 15, HB2 exhibited favorable corrosion resistance in all of the samples. Also, HC276 exhibited corrosion resistance sufficient for use, though not to the extent of HB2. HC276 was usable depending on a condition at 165° C. and was at a usable level at 160° C. SUS316 was usable under the conditions of Examples 5 to 15 involving a temperature of not more than 155° C., was usable depending on a condition at 160° C. and was not usable at a temperature of more than 165° C. Through all of the conditions, the composition contaminated with potassium acetate in Examples 3, 7, and 11 tends to slightly worsen corrosiveness as compared with corrosion data obtained at the same temperatures thereas on pure acetic acid alone in Comparative Example 2 and Examples 2, 6, 10, and 14. Rather, it is evident that corrosion is remarkably influenced by a temperature. The composition contaminated with acetic anhydride in Examples 4, 8, and 12 had slightly larger influence on the corrosion rate than that in the pure acetic acid data. The composition contaminated with propionic acid in Comparative Example 1 and Examples 1, 5, 9, and 13 was at a level equivalent to pure acetic acid.

All of the conditions except for Comparative Example 2 and Examples 2, 6, 10, and 14 lead to a boiling point at the same pressure on the order of 90 kPa. Under the same operating pressure, the corrosion rate is reduced with respect to pure acetic acid with decrease in the concentration of potassium acetate, acetic anhydride, or propionic acid resulting in a rise in boiling point. Also, even for pure acetic acid, corrosion is increased as the boiling point is elevated by a rise in pressure. Therefore, operation using a proper and economic material having corrosion resistance is achieved by combining the concentration control of higher boiling point impurities with operating pressure control. It was also found that the corrosion rate differs slightly depending on contaminating impurities even at the same temperature. Accordingly, equipment made of a lower material can be designed by performing not only temperature control based on pressure control but the control of impurity concentrations themselves and thereby reducing the corrosion rate.

At a lower operating pressure, an operating temperature is decreased so that corrosiveness is reduced. However, since gas density is decreased, the column diameter of a distillation column, etc., is increased, resulting in diseconomy. Accordingly, it is preferred to set the lower limit of the operating pressure, from the viewpoint of economy.

In general, the prices of the materials are decreased in the order of Zr>HB2>HC276>SUS, and their corrosion resistance is also reduced in this order. A guideline for corrosion rates and material selection is as described below. The following criteria are given for a mere guideline and vary depending on the initial thickness of a material and the frequency of renewal.

Less than 0.05 mm/Y: suitable for use
0.05 to 0.1 mm/Y: at a usable level
0.1 mm/Y to 0.2 mm/Y: usable depending on a condition
More than 0.2 mm/Y: unsuitable for use The configurations according to the present invention and variations or modifications thereof will be listed below as a summary of the above description.

Appendix 1: A method for producing acetic acid, comprising the step of distilling a crude acetic acid solution containing acetic acid and an impurity having a higher boiling point than that of acetic acid to purify the acetic acid, wherein the distillation of the crude acetic acid solution is performed under a condition involving a column bottom temperature of a distillation column of not more than 165° C. (preferably not more than 155° C., more preferably not more than 150° C., further preferably not more than 140° C.)

Appendix 2: The method for producing acetic acid according to appendix 1, wherein an acetic acid concentration in the crude acetic acid solution is not less than 90% by mass (e.g., not less than 95% by mass, preferably not less than 97% by mass, more preferably not less than 98% by mass, further preferably not less than 99% by mass).

Appendix 3: The method for producing acetic acid according to appendix 1 or 2, wherein the impurity having a higher boiling point than that of acetic acid comprises at least one compound selected from the group consisting of an acetate salt, acetic anhydride, and propionic acid.

Appendix 4: The method for producing acetic acid according to any one of appendixes 1 to 3, wherein an acetate salt concentration of a column bottom fraction of the distillation column is not more than 34% by mass (preferably not more than 23% by mass, more preferably not more than 13% by mass, further preferably not more than 10% by mass, particularly preferably not more than 1% by mass).

Appendix 5: The method for producing acetic acid according to any one of appendixes 1 to 4, wherein an acetic anhydride concentration of the column bottom fraction of the distillation column is not more than 90% by mass (preferably not more than 74% by mass, more preferably not more than 45% by mass, further preferably not more than 10% by mass, particularly preferably not more than 1% by mass).

Appendix 6: The method for producing acetic acid according to any one of appendixes 1 to 5, wherein a propionic acid concentration of the column bottom fraction of the distillation column is not more than 90% by mass (preferably not more than 75% by mass, more preferably not more than 55% by mass, further preferably not more than 29% by mass, particularly preferably not more than 10% by mass, in particular, not more than 1% by mass).

Appendix 7: The method for producing acetic acid according to any one of appendixes 1 to 6, wherein the distillation is performed under a condition involving a column bottom pressure of the distillation column of less than 0.255 MPaG (preferably not more than 0.24 MPaG, further preferably not more than 0.23 MPaG, particularly preferably not more than 0.21 MPaG).

Appendix 8: The method for producing acetic acid according to appendix 7, wherein the distillation is performed under a condition involving a column bottom pressure of the distillation column of not less than 0.01 MPaG (preferably not less than 0.02 MPaG, further preferably not less than 0.03 MPaG, particularly preferably not less than 0.05 MPaG).

Appendix 9: The method for producing acetic acid according to any one of appendixes 1 to 8, wherein the distillation is performed under a condition involving a column bottom pressure of the distillation column of not less than 0.01 MPaG and less than 0.255 MPaG.

Appendix 10: The method for producing acetic acid according to any one of appendixes 1 to 9, wherein the method comprises a carbonylation reaction step of reacting methanol with carbon monoxide to produce acetic acid, an evaporation step of separating the reaction mixture obtained in the carbonylation reaction step into a vapor stream and a residual liquid stream, a lower boiling point component removal step of separating the vapor stream by distillation into an overhead stream rich in lower boiling point component and an acetic acid stream (first acetic acid stream) rich in acetic acid, and an acetic acid distillation step of distilling the acetic acid stream to purify the acetic acid, wherein the acetic acid distillation step has at least one step of performing the distillation of the crude acetic acid solution under a condition involving a column bottom temperature of the distillation column of not more than 165° C.

Appendix 11: The method for producing acetic acid according to appendix 10, wherein potassium hydroxide is fed or added to the first acetic acid stream via a potassium hydroxide introduction line.

Appendix 12: The method for producing acetic acid according to appendix 10 or 11, wherein the acetic acid distillation step has at least one distillation step in which an acetic acid concentration in the crude acetic acid solution to be subjected to the distillation is not less than 97% by mass, and in all of such steps, the distillation of the crude acetic acid solution is performed under a condition involving a column bottom temperature of the distillation column of not more than 165° C. (preferably not more than 155° C., more preferably not more than 150° C., further preferably not more than 140° C.)

Appendix 13: The method for producing acetic acid according to any one of appendixes 10 to 12, wherein the acetic acid distillation step comprises a dehydration step of separating the first acetic acid stream by distillation into a second acetic acid stream more enriched with acetic acid than the first acetic acid stream, and a vapor of an overhead stream containing a larger amount of a component having a lower boiling point than that of acetic acid as compared with the second acetic acid stream.

Appendix 14: The method for producing acetic acid according to appendix 13, wherein the distillation of the first acetic acid stream is performed under a condition involving a column bottom temperature of a distillation column of not more than 165° C. (preferably not more than 155° C., more preferably not more than 150° C., further preferably not more than 140° C.)

Appendix 15: The method for producing acetic acid according to appendix 13 or 14, wherein potassium hydroxide is fed or added to the second acetic acid stream via a potassium hydroxide introduction line.

Appendix 16: The method for producing acetic acid according to any one of appendixes 13 to 15, wherein the acetic acid distillation step comprises a higher boiling point component removal step of separating the second acetic acid stream by distillation into a vapor as an overhead stream containing a larger amount of a component having a lower boiling point than that of acetic acid as compared with a bottom fraction, the bottom fraction containing a larger amount of a component having a higher boiling point than that of acetic acid as compared with the overhead stream, and a third acetic acid stream more enriched with acetic acid than the second acetic acid stream.

Appendix 17: The method for producing acetic acid according to appendix 16, wherein the distillation of the second acetic acid stream is performed under a condition involving a column bottom temperature of a distillation column of not more than 165° C. (preferably not more than 155° C., more preferably not more than 150° C., further preferably not more than 140° C.)

Appendix 18: The method for producing acetic acid according to appendix 17, wherein an acetate salt concentration in the column bottom fraction of the distillation column in the higher boiling point component removal step is 1 ppm by mass to 34% by mass (preferably 100 ppm by mass to 25% by mass, further preferably 0.1 to 20% by mass (e.g., 1 to 15% by mass)).

Appendix 19: The method for producing acetic acid according to appendix 18, wherein the acetate salt concentration in the column bottom fraction of the distillation column in the higher boiling point component removal step is lowered by decreasing the amount of an alkali added for use in the neutralization of hydrogen iodide.

Appendix 20: The method for producing acetic acid according to any one of appendixes 17 to 19, wherein an acetic anhydride concentration in the column bottom fraction of the distillation column in the higher boiling point component removal step is 1 ppm by mass to 91% by mass (preferably 10 ppm by mass to 74% by mass, more preferably 100 ppm by mass to 44% by mass, further preferably 0.1 to 20% by mass, particularly preferably 0.2 to 10% by mass (e.g., 0.5 to 5% by mass)).

Appendix 21: The method for producing acetic acid according to appendix 20, wherein the acetic anhydride concentration in the column bottom fraction of the distillation column in the higher boiling point component removal step is lowered by hydrolyzing the acetic anhydride by the addition of water into piping or an apparatus positioned upstream of the distillation column, or into the distillation column.

Appendix 22: The method for producing acetic acid according to any one of appendixes 17 to 21, wherein a propionic acid concentration in the column bottom fraction of the distillation column in the higher boiling point component removal step is 100 ppm by mass to 91% by mass (preferably 0.1 to 75% by mass, more preferably 0.3 to 55% by mass, further preferably 0.5 to 29% by mass, particularly preferably 1 to 15% by mass).

Appendix 23: The method for producing acetic acid according to appendix 22, wherein the propionic acid concentration in the column bottom fraction of the distillation column in the higher boiling point component removal step is lowered by not less than 1 method selected from the group consisting of reduction in the production of the by-product propionic acid in a reaction vessel by changing reaction conditions, separation and removal of acetaldehyde responsible for the production of the by-product propionic acid from a process solution during recycle of a portion of the process solution to the reaction system, followed by recycle to the reaction system, and disposition of a distillation column or an evaporator for propionic acid separation and removal upstream of the distillation column.

Appendix 24: The method for producing acetic acid according to any one of appendixes 16 to 23, further comprising an ion exchange resin treatment step of introducing the third acetic acid stream to an ion exchange resin column so that an alkyl iodide in the third acetic acid stream is adsorptively removed to obtain a fourth acetic acid stream.

Appendix 25: The method for producing acetic acid according to appendix 24, further comprising the step of distilling the fourth acetic acid stream under a condition involving a column bottom temperature of a product column (distillation column) of not more than 165° C. to obtain purified acetic acid.

Appendix 26: The method for producing acetic acid according to appendix 25, wherein an acetate salt concentration in a column bottom fraction of the product column is 0.1 ppb by mass to 1% by mass (preferably 1 ppb by mass to 0.1% by mass, further preferably 10 ppb by mass to 0.01% by mass (e.g., 100 ppb by mass to 0.001% by mass)).

Appendix 27: The method for producing acetic acid according to appendix 26, wherein the acetate salt concentration in the column bottom fraction of the product column is lowered by decreasing the amount of an alkali added for use in the neutralization of hydrogen iodide.

Appendix 28: The method for producing acetic acid according to any one of appendixes 25 to 27, wherein an acetic anhydride concentration in the column bottom fraction of the product column is 0.1 ppm by mass to 60% by mass (preferably 1 ppm by mass to 10% by mass, further preferably 10 ppm by mass to 2% by mass (e.g., 50 ppm by mass to 0.5% by mass).

Appendix 29: The method for producing acetic acid according to any one of appendixes 25 to 27, wherein the acetic anhydride concentration in the column bottom fraction of the product column is 0.2 to 10% by mass (e.g., 0.5 to 5% by mass).

Appendix 30: The method for producing acetic acid according to appendix 28 or 29, wherein the acetic anhydride concentration in the column bottom fraction of the product column is lowered by hydrolyzing the acetic anhydride by the addition of water into piping or an apparatus positioned upstream of the product column, or into the product column.

Appendix 31: The method for producing acetic acid according to any one of appendixes 25 to 30, wherein a propionic acid concentration in the column bottom fraction of the product column is 1 ppm by mass to 10% by mass (preferably 10 ppm by mass to 5% by mass, further preferably 50 ppm by mass to 1% by mass (e.g., 100 ppm by mass to 0.1% by mass)).

Appendix 32: The method for producing acetic acid according to appendix 31, wherein the propionic acid concentration in the column bottom fraction of the product column is lowered by not less than 1 method selected from the group consisting of reduction in the production of the by-product propionic acid in a reaction vessel by changing reaction conditions, separation and removal of acetaldehyde responsible for the production of the by-product propionic acid from a process solution during recycle of a portion of the process solution to the reaction system, followed by recycle to the reaction system, and disposition of a distillation column or an evaporator for propionic acid separation and removal upstream of the product column.

Appendix 33: The method for producing acetic acid according to any one of appendixes 1 to 32, wherein a material for the distillation column is at least one material selected from the group consisting of a nickel-based alloy, stainless steel, aluminum, and titanium.

Appendix 34: The method for producing acetic acid according to any one of appendixes 1 to 33, wherein the column bottom fraction of the distillation column has an acetate salt concentration of not more than 34% by mass, an acetic anhydride concentration of not more than 90% by mass, and a propionic acid concentration of not more than 90% by mass, the column bottom pressure of the distillation column is less than 0.255 MPa, the material for the distillation column is at least one material selected from the group consisting of a nickel-based alloy, stainless steel, aluminum, and titanium, and the column bottom temperature is less than 165° C.

INDUSTRIAL APPLICABILITY

The method for producing acetic acid of the present invention can be used as industrial method for producing acetic acid by carbonylation process of a methanol method (acetic acid process of a methanol method).

REFERENCE SIGNS LIST

1: reaction vessel
2: evaporator
3, 5, and 6: distillation column
4: decanter
7: ion exchange resin column
8: scrubber system
9: acetaldehyde separation and removal system
16: reaction mixture feed line
17: vapor stream discharge line
18 and 19: residual liquid stream recycle line
54: carbon monoxide-containing gas introduction line
55 and 56: potassium hydroxide introduction line
57: catalyst circulating pump
91: distillation column (first acetaldehyde removal column)
92: extraction column
93: distillation column (second acetaldehyde removal column)
94: distillation column (extractive distillation column)
95: decanter
96: decanter
97: distillation column (acetaldehyde removal column)
98: distillation column (extractive distillation column)
99: decanter
200: chimney tray

The invention claimed is:

1. A method for producing acetic acid, comprising distilling a crude acetic acid solution containing acetic acid and an impurity having a higher boiling point than that of acetic acid to purify the acetic acid, wherein the method comprises
carbonylating methanol with carbon monoxide to produce acetic acid,
evaporating a reaction mixture obtained by the carbonylation to separate into a vapor stream and a residual liquid stream,
removing a lower boiling point component by distillation to separate the vapor stream into an overhead stream rich in lower boiling point component and a first acetic acid stream rich in acetic acid, dehydrating the first acetic acid stream by distillation to separate into a second acetic acid stream more enriched with acetic acid than the first acetic acid stream, and a vapor of an overhead stream containing a larger amount of a component having a lower boiling point than that of acetic acid as compared with the second acetic acid stream, and removing a higher boiling point component by distillation to separate the second acetic acid stream into a vapor as an overhead stream containing a larger amount of a component having a lower boiling point than that of acetic acid as compared with a bottom fraction, the bottom fraction containing a larger amount of a component having a higher boiling point than that of acetic acid as compared with the overhead stream, and a third acetic acid stream more enriched with acetic acid than the second acetic acid stream; and wherein the distillation of the second acetic acid stream is performed under a condition involving a column bottom temperature of a distillation column of 70 to 165° C. and a column bottom pressure of the distillation column of not less than 0.01 MPaG and less than 0.255 MPaG, and the bottom fraction of the distillation column has an acetate salt concentration of not more than 34% by mass, an acetic anhydride concentration of not more than 90% by mass, and a propionic acid concentration of not more than 90% by mass.

2. The method for producing acetic acid according to claim 1, wherein an acetic acid concentration in the second acetic acid stream is not less than 90% by mass.

3. The method for producing acetic acid according to claim 1, wherein the impurity having a higher boiling point than that of acetic acid comprises at least one compound selected from the group consisting of an acetate salt, acetic anhydride, and propionic acid.

4. The method for producing acetic acid according to claim 1, further comprising distilling the acetic acid stream to purify the acetic acid, comprising at least one distillation in which an acetic acid concentration in the crude acetic acid solution to be subjected to the distillation is not less than 97% by mass, and in all distillations, the distillation of the crude acetic acid solution is performed under a condition involving a column bottom temperature of the distillation column of not more than 165° C.

5. The method for producing acetic acid according to claim 1, wherein a material for the distillation column is at least one material selected from the group consisting of a nickel-based alloy, stainless steel, aluminum, and titanium.

6. The method for producing acetic acid according to claim 1, wherein potassium hydroxide is fed or added to the first acetic acid stream via a potassium hydroxide introduction line.

7. The method for producing acetic acid according to claim 1, wherein the distillation of the first acetic acid stream is performed under a condition involving a column bottom temperature of a distillation column of not more than 165° C.

8. The method for producing acetic acid according to claim 1, wherein potassium hydroxide is fed or added to the second acetic acid stream via a potassium hydroxide introduction line.

9. The method for producing acetic acid according to claim 1, wherein the distillation of the second acetic acid stream is performed under a condition involving a column bottom temperature of a distillation column of not more than 155° C.

10. The method for producing acetic acid according to claim 1, wherein the acetate salt concentration in the bottom fraction is 1 ppm by mass to 34% by mass.

11. The method for producing acetic acid according to claim 1, wherein the acetate salt concentration in the bottom fraction is 100 ppm by mass to 25% by mass.

12. The method for producing acetic acid according to claim 1, wherein the acetate salt concentration in the bottom fraction is lowered by decreasing the amount of an alkali added for use in the neutralization of hydrogen iodide.

13. The method for producing acetic acid according to claim 1, wherein the acetic anhydride concentration in the bottom fraction is 10 ppm by mass to 74% by mass.

14. The method for producing acetic acid according to claim 1, wherein the acetic anhydride concentration in the bottom fraction is lowered by hydrolyzing the acetic anhydride by the addition of water into piping or an apparatus positioned upstream of the distillation column, or into the distillation column.

15. The method for producing acetic acid according to claim 1, wherein the propionic acid concentration in the bottom fraction is 100 ppm by mass to 91% by mass.

16. The method for producing acetic acid according to claim 1, further comprising introducing the third acetic acid stream to an ion exchange resin column so that an alkyl iodide in the third acetic acid stream is removed to obtain a fourth acetic acid stream.

17. The method for producing acetic acid according to claim 16, further comprising distilling the fourth acetic acid stream under a condition involving a column bottom temperature of a product column of not more than 165° C. to obtain purified acetic acid.

18. The method for producing acetic acid according to claim 17, wherein an acetate salt concentration in a column bottom fraction of the product column is 0.1 ppb by mass to 1% by mass.

19. The method for producing acetic acid according to claim 17, wherein an acetic anhydride concentration in the column bottom fraction of the product column is 0.1 ppm by mass to 60% by mass.

20. The method for producing acetic acid according to claim 17, wherein a propionic acid concentration in the column bottom fraction of the product column is 1 ppm by mass to 10% by mass.

* * * * *